(12) United States Patent
Bobrowicz

(10) Patent No.: US 7,465,577 B2
(45) Date of Patent: Dec. 16, 2008

(54) METHODS FOR REDUCING OR ELIMINATING α-MANNOSIDASE RESISTANT GLYCANS FOR THE PRODUCTION OF GLYCOPROTEINS

(75) Inventor: Piotr Bobrowicz, White River Junction, VT (US)

(73) Assignee: GlycoFi, Inc., Lebanon, NH (US)

( * ) Notice: Subject to any disclaimer, the term of this patent is extended or adjusted under 35 U.S.C. 154(b) by 209 days.

(21) Appl. No.: 11/118,008

(22) Filed: Apr. 29, 2005

(65) Prior Publication Data

US 2006/0211085 A1    Sep. 21, 2006

Related U.S. Application Data

(60) Provisional application No. 60/620,186, filed on Oct. 18, 2004.

(51) Int. Cl.
C12N 1/14 (2006.01)
C12N 1/15 (2006.01)
C12N 15/09 (2006.01)

(52) U.S. Cl. ............................. 435/255.5; 435/254.23; 435/69.1

(58) Field of Classification Search ....................... None
See application file for complete search history.

(56) References Cited

U.S. PATENT DOCUMENTS

| 7,029,872 B2 * | 4/2006 | Gerngross | 435/69.1 |
| 2004/0018590 A1 | 1/2004 | Gerngross et al. | |
| 2006/0160179 A1 | 7/2006 | Bobrowicz et al. | |

FOREIGN PATENT DOCUMENTS

EP    1283265    *    2/2003

OTHER PUBLICATIONS

Cutler, Med. Mycology, vol. 39 (2001), pp. 75-86, "N-Glycosylation of yeast, with emphasis on candida albicans".
Shibata et al., Arch. Biochem. & Biophys., vol. 243 (1985), pp. 338-348, "Immunochemical study on the mannans of *Candida albicans* NIH A-207, . . . ".
Shibata et al., Arch. Biochem. & Biophys., vol. 302 (1993), pp. 113-117, "Complete assignment of 1H and 13C nuclear magnetic resonance chemical shifts of beta-1,2-linked mannooligosaccharides . . . ".
Kobayashi et al., Arch. Biochem. & Biophys., vol. 294 (1992), pp. 662-669, "Sructural study of a cell wall mannan-protein complex of the pathogenic yeast *Candida glabrata* . . . ".
Han et al., Infection & Immunity, vol. 65 (1997), pp. 4100-4107, "Biochemical characterization of *Candida albicans* epitopes that can elicit protective and nonprotective antibodies".
Kobayashi et al., Infection & Immunity, vol. 62 (1994), pp. 968-973, "Structural modification of cell wall mannans of *Candida albicans* Serotype A strains grown in yeast extract-Sabouraud liquid medium . . . ".
Kobayashi et al., Arch. Biochem. & Biophysics, vol. 272 (1989), pp. 365-375, "Structural study of phosphomannan of yeast-form cells of *Candida albicans* J-1012 strain . . . ".
Kobayashi et al., Arch. Biochem. & Biophysics, vol. 245 (1986), pp. 494-503, "Acetolysis of *Pichia pastoris* IFO 0948 strain mannan containing alpha-1,2 and beta-1,2 linkages using acetolysis medium of low sulfuric acid concentration".
Jouault et al., Clin. Diagnos. Lab. Immun., vol. 4 (1997), pp. 328-333, "Differential humoral reponse against alpha- and beta-linked mannose residues associated with tissue invasion by *Candida albicans*".
Cregg et al., Mol. Biotech., vol. 16 (2000), pp. 23-52, "Recombinant protein expression in *Pichia pastoris*".
Choi et al., PNAS, vol. 100 (2003), pp. 5022-5027, "Use of combinatorial genetic libraries to humanize N-linked glycosylation in the yeast *Pichia pastoris*".
Ziegler et al., Glycobiology, vol. 9 (1999), pp. 497-505, "Novel schizosaccharomyces pombe N-linked GalMan9GlcNAc isomers: role of the Golgi GMA 12 galactosyltransferase . . . ".
Trimble et al., Glycobiology, vol. 14 (2004), pp. 265-274, "Characterization of N- and O-linked glycosylation of recombinant human bile salt-stimulated lipase secreted by *Pichia pastoris*".
Suzuki et al., J. Biol. Chem., vol. 272 (1997), pp. 16822-16828, "Characterization of beta-1,2-mannosyltransferase in *Candida guilliermondii* and its utilization . . . ".
Rosenfeld et al., J. Biol. Chem., vol. 249 (1974), pp. 2319-2321, "Genetic control of yeast mannan structure".
Shibata et al., Eur. J. Biochem., vol. 217 (1993), pp. 1-12, "Structural study of cell-wall mannan of *Saccharomyces kluyveri* IFO 1685 strain ".
Takeuchi, Trends in Glycosci. & Glycotech., vol. 9 (1997), pp. S29-S35, "Trial for molecularbgreeding of yeast for the production of glycoprotein therapeutics".
Genbank No. P36044, Glycobiol., vol. 6 (1996), pp. 805-810, "Cloning and analysis of the MNN4 gene required for phosphorylation of N-linked oligosaccharides in *Saccharomyces cerevisiae*".

* cited by examiner

*Primary Examiner*—Nancy Vogel
(74) *Attorney, Agent, or Firm*—John David Reilly; Catherine D. Fitch; William Krovatin

(57) ABSTRACT

The present invention provides methods to reduce or eliminate α-mannosidase resistant glycans on glycoproteins in yeast. The reduction or elimination of α-mannosidase resistant glycans on glycoproteins results from the disruption of the newly isolated *P. pastoris* AMR2 gene encoding β1,2-mannosyltransferase. The present invention also discloses novel genes, polypeptides, antibodies, vectors and host cells relating to α-mannosidase resistance on glycans.

8 Claims, 11 Drawing Sheets

FIG. 1A

```
  1 ATG AGA ACA CGA AAC TTC CTG CTC TGT ATT GCC AGT GTT TTG TCT GTG ATT TGG ATC GTC CTT ACT
  1 ▸Met Arg Thr Arg Asn Phe Leu Leu Cys Ile Ala Ser Val Leu Ser Val Ile Trp Ile Val Leu Thr

79 TGG AAT GAT AAT CTT GGC GGA ATC TCC CTA AAC GGA GGC AAG GAT TCT GCC TAT GAT CTG CTA TTG GGA
 27 ▸Trp Asn Asp Asn Leu Gly Gly Ile Ser Leu Asn Gly Gly Lys Asp Ser Ala Tyr Asp Leu Leu Ser Leu Gly

157 AGC TTC AAC GAC ATG GAG GTC GAC TCC GAC TAT GTC AAC ATC TAC AAT GCT CCA GTG CTA GGA TGT ACG GAT TTG
 53 ▸Ser Phe Asn Asp Met Glu Val Asp Ser Asp Tyr Val Asn Ile Tyr Asn Ala Pro Val Leu Gly Cys Thr Asp Leu

235 TCT TAT CAT GGA TTG TTG CTG AAA GTC ACC CCA AAG CAT GAC TTA GCT TTG GAG TTC ATA AGA GCT CAG ATT TTG
 79 ▸Ser Tyr His Gly Leu Leu Leu Lys Val Thr Pro Lys His Asp Leu Ala Leu Glu Phe Ile Arg Ala Gln Ile Leu

313 GAC ATT GAC GTT TAC TCC GCC ATA AAA GAC TTA GAA GAT CTG AAA AAG GCC TTG ACT GTA CAA AAG GTT GAA AAA CAC TGG
105 ▸Asp Ile Asp Val Tyr Ser Ala Ile Lys Asp Leu Glu Asp Leu Lys Lys Ala Leu Thr Val Gln Lys Val Glu Lys His Trp

391 TTT ACG TTT TAT GGT AGT TCA GTC TTT CTG CCC GAA GTG CAT GTG CAT GTG CAG GAA GTC GTT AGA CGA GTC ATC TTT TCG GCT
131 ▸Phe Thr Phe Tyr Gly Ser Ser Val Phe Leu Pro Glu Val His Asp His Gln Glu Val Val Arg Arg Val Ile Phe Ser Ala

469 GAA GGA AAG GCG AAC TCT CCA GTA ACA TCT ATC ATA GTT GCT CAG ATA TAT GAC AAA AAC TGG AAC GAG TTA AAT GGC
157 ▸Glu Gly Lys Ala Asn Ser Pro Val Thr Ser Ile Ile Val Ala Gln Ile Tyr Asp Lys Asn Trp Asn Glu Leu Asn Gly

547 CAT TTC TTG GAC ATC CTG AAC CCA AAT ACT GGG AAG GTC CAG CAC CAC TTT CCA CAA GTT CTT CCT ATT GCA ACC
183 ▸His Phe Leu Asp Ile Leu Asn Pro Asn Thr Gly Lys Val Gln His His Asn Thr Phe Pro Gln Val Leu Pro Ile Ala Thr

625 AAT TTT GTC AAA GGT AAG AAG TTT CGT GGG GCA GAA GAT CCT AGA GTT GTT TTG AGA AAG GGC CGT TTT GGA CCT GAT
209 ▸Asn Phe Val Lys Gly Lys Lys Phe Arg Gly Ala Glu Asp Pro Arg Val Val Leu Arg Lys Gly Arg Phe Gly Pro Asp

703 CCT TTG GTG ATG TTC AAC TCC CTA ACT CAA GAT AAC CGT AGG AGA ATT TCT CCA TTT GAC CAG TTC
235 ▸Pro Leu Val Met Phe Asn Ser Leu Thr Gln Asp Asn Arg Arg Arg Ile Ser Pro Phe Asp Gln Phe

781 AAA ACA GAG ATG TAC GAC ATT AAA GAC TAT GAG ATG CCC AGC TAT GAA AAG TGG CCA GTC CCA TTT TTC TTA AAA GAC
261 ▸Lys Thr Glu Met Tyr Asp Ile Lys Asp Tyr Glu Met Pro Arg Tyr Glu Lys Trp Pro Val Pro Phe Phe Leu Lys Asp

859 AAT CAG GAG ATG GCA GTT CAT CAT TTT GTT TAC TCT TTC AAC CCT CTG AGA GTA CTC AAA TGC AGT CTT GAT GAC GGC TCA TGT
287 ▸Asn Gln Glu Met Ala Val His Phe Val Tyr Ser Phe Asn Pro Leu Arg Val Leu Lys Cys Ser Leu Asp Asp Gly Ser Cys

937 GAT ATT GTG GAG ATA CCG AAA GTT GAC TCG TCT GAG TTG CGT GGT GCC ACA CCT ATG ATC AAT CTT CCT
313 ▸Asp Ile Val Glu Ile Pro Lys Val Asp Ser Ser Glu Leu Arg Gly Ala Thr Pro Met Ile Asn Leu Pro
```

FIG. 1B

```
1015 CAG GCA ATT CCG ATG GCG AAG GAC ATC TGG GTT TCA TTC CCC AGA ACG AGA ATT GCA AAT TGT GGT TGC TCC
 339 ▷Gln Ala Ile Pro Met Ala Lys Asp Ile Trp Val Ser Phe Pro Arg Thr Arg Ile Ala Asn Cys Gly Cys Ser

1093 AGG ACG ACA TAC AGA CCA ATG CTG ATG TTT GTC ATG GAA GGT TCA GAA GAC TTC TTT GTT GAA CTC TTG TCC ACC TCT
 365 ▷Arg Thr Thr Tyr Arg Pro Met Leu met Leu Phe Val Arg Glu Gly Ser Glu Asp Phe Phe Val Glu Leu Leu Ser Thr Ser 1171 CTT GAT TTT GGT CTG GAG GTT TTA CCG TAT CTG GAA AAC GGA TTA CCA TGC AGT GCG GAC CAT TCC GTT TTA ATC CCA
 391 ▷Leu Asp Phe Gly Leu Glu Val Leu Pro Tyr Leu Glu Asn Gly Leu Pro Cys Ser Ala Asp His Ser Val Leu Ile Pro 1249 AAT AGC ATT GAT AAC TGG GAA GTC GTA GAT GCT AAT GGA GTC GTA GAT GCT AAT TTG TCA TTC GAG GCG GAC AAG
 417 ▷Asn Ser Ile Asp Asn Trp Glu Val Val Asp Ala Asn Gly Asp Asp Ile Leu Thr Leu Ser Phe Ser Glu Ala Asp Lys 1327 AGT ACC TCT GTG ATT CAT ATC AGA GGG CTG TAT CTA TCT GAA CTG CTA GAT GGT CAA GGT TAT CAA GGT TAT CAA GGT CCA GAA GCA GAG
 443 ▷Ser Thr Ser Val Ile His Ile Arg Gly Leu Tyr Leu Ser Glu Leu Asp Gly Tyr Gln Gly Pro Glu Ala Glu 1405 GAT GAA CAT AAT TTC CAG CGT ATC CTG AGT GAC TTA CAT TTT GAC AAC AAA ACG GTA AAC AAT TTT ATA AAA GTA
 469 ▷Asp Glu His Asn Phe Gln Arg Ile Leu Ser Asp Leu His Phe Asp Asn Lys Thr Val Asn Asn Phe Ile Lys Val 1483 CAA TCA TGT GCA CTA GAT GCT GCC AAA GGT TAT TGT AAA GAA TAT GGG CTT ACT CGT GGG GCA GAA CGA AGA AGG
 495 ▷Gln Ser Cys Ala Leu Asp Ala Ala Lys Gly Tyr Cys Lys Glu Tyr Gly Leu Thr Arg Gly Ala Glu Arg Arg Arg 1561 AGG GTC GCT GAG GAG AGA GAA CAA AAG GAA AAG AAG AAG AAG GAG AAA GAG GAA GAA GAA AAA GAG GAA GAA GAG
 521 ▷Arg Val Ala Glu Glu Arg Glu Gln Lys Glu Lys Lys Lys Lys Glu Lys Glu Glu Glu Lys Glu Glu Glu Glu 1639 AAA AAG AGG ATT GAA GAG ATC GAG GAG GAG AAG AAG AAG GAG CGA AAG GAG AAA GAG GAA GAA GCG GAG AGA
 547 ▷Lys Lys Arg Ile Glu Glu Ile Glu Glu Glu Lys Lys Lys Glu Arg Lys Glu Lys Glu Glu Lys Glu Ala Glu Arg 1717 AAA AAG CTG CAA GAA ATG AAA AAG AAG AAG AAA CTT GAG GAA ATC ACA GAA AAA CTT GAA GGC CAG AGG AAT AAA GAG ATA
 573 ▷Lys Lys Leu Gln Glu Met Lys Lys Lys Lys Leu Glu Glu Ile Thr Glu Lys Leu Glu Gly Gln Arg Asn Lys Glu Ile 1795 GAT CCA AAA GAG AAG CAA GAG GAA GAA AGA AAG GAG GTC AGG AGA GTC AGG GTC AGG AAA CAA AGG AAG GAG
 599 ▷Asp Pro Lys Glu Lys Gln Glu Glu Glu Arg Lys Glu Val Arg Val Arg Lys Glu Lys Gln Arg Lys Glu 1873 GCG GAA AAG GAG GCT GAA AAA AAG GAG CTA AAA GAT CTA AAA AAG GAT CTA AAA AAG GAT CTA AAA ATA AGA CAG TAG
 625 ▷Ala Glu Lys Glu Ala Glu Lys Lys Asp Leu Lys Lys Asp Leu Lys Ile Ala Glu Ile Arg Gln ...
```

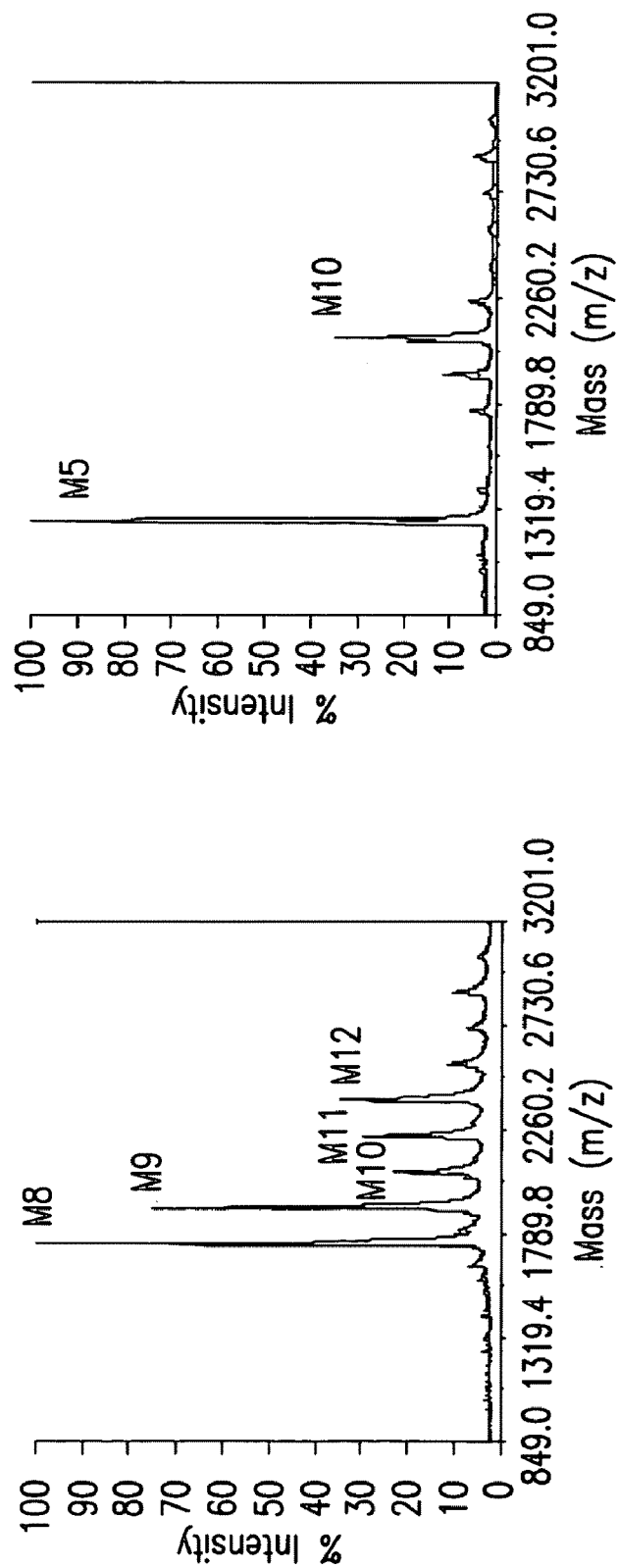

```
601 KEKQREEEERKERVRKIAEKQRKEAEKKEAEKKANDKKDLKIRQ      AMR2p
619 K-------KKIIVEKLA-KEQEEAEKLEAKKKLYQLQE-EERS       AMR1p
592 KAK                                               AMR3p
501 ------------------------------------ELH           AMR4p
737 DEDDKEKNDESGLTEKSEVEENGENTSEGSEGEEEDDDDIEV        CaORF1
694                                                   CaORF2
654                                                   CaORF3
646                                                   CaORF4
612                                                   CaORF5
650 ---------------------------------------ET        CaORF6
590                                                   CaORF7
684                                                   CaORF8
```

FIG.5E

METHODS FOR REDUCING OR ELIMINATING α-MANNOSIDASE RESISTANT GLYCANS FOR THE PRODUCTION OF GLYCOPROTEINS

CROSS-REFERENCE TO RELATED APPLICATIONS

This application claims priority to U.S. provisional application Ser. No. 60/620,186 filed on Oct. 18, 2004.

FIELD OF THE INVENTION

The present invention relates to the field of protein glycosylation engineering in lower eukaryotes. The present invention further relates to engineering of yeast and filamentous fungal host cells for the production of therapeutic glycoproteins. In particular, the present invention relates to the reduction or elimination of α-mannosidase resistant glycans on glycoproteins, and methods for reducing or eliminating a gene involved in the production of α-mannosidase resistance on glycans in yeast cells.

BACKGROUND OF THE INVENTION

The ability to produce recombinant human proteins has led to major advances in human health care and remains an active area of drug discovery. Many therapeutic proteins require the posttranslational addition of glycans to specific asparagine residues (N-glycosylation) of the protein to ensure proper structure-function activity and subsequent stability in human serum. For therapeutic use in humans, glycoproteins require human-like N-glycosylation. Mammalian cell lines (e.g., CHO cells, human retinal cells) that can mimic human-like glycoprotein processing have several drawbacks including low protein titers, long fermentation times, heterogeneous products, and continued viral containment. It is therefore desirable to use an expression system that not only produces high protein titers with short fermentation times, but can also produce human-like glycoproteins.

Fungal hosts such as the methylotrophic yeast *Pichia pastoris* has distinct advantages for therapeutic protein expression—e.g. it does not secrete high amounts of endogenous proteins, it has a strong inducible promoter, it can be grown in defined chemical media, and it can produce high titers of recombinant proteins (Cregg et al., 2000). However, glycosylated proteins expressed in *P. pastoris* contain additional mannose sugars resulting in "high mannose" glycans, as well as mannosylphosphate groups which impart a negative charge onto glycoproteins. Glycoproteins with either high mannose glycans or charged mannans are a high risk for illiciting an immune response in humans (Takeuchi, 1997; Rosenfeld and Ballou, 1974). Accordingly, it is desirable to produce therapeutic glycoproteins in fungal host systems, such that the pattern of glycosylation is identical or at least similar to that in humans.

Some fungal hosts contain immunogenic β-mannosylation on glycans of glycoproteins. In order to circumvent antigenicity, it is desirable to eliminate β-mannosylation in the production of human-like glycoproteins. Oligomannosides with β-1,2-linkage were first described by Shibata et al., (1985) in association with *Candida albicans* cell wall phosphopeptidomannan by phosphodiester bridges. Subsequently, three types of β-1,2 linkages have been identified in the side chains of *Candida* cell wall mannans. The first is a β-1,2-linked manno-oligomer located in a phosphodiesterified oligosaccharide moiety which is a common epitope in the mannans of several *Candida* species (Shibata et al 1993a). The second type is a β-1,2-linked mannose unit attached to the nonreducing terminal of the α-1,2 oligomannosyl side chains in the mannans of *Candida albicans, tropicalis* and *glabrata* (Kobayashi et al., 1989, 1992 and 1994). The third type of β-1,2 linkage is found in *Candida guilliemondii* and contains β-1,2 linked mannose units attached to an α-1,3 linked mannose unit (Shibata et al., 1993b). Despite these findings, the studies on β-1,2 linkages have been limited by unsuccessful attempts to identify a β-1,2 mannosyl-transferase gene. Suzuki et al., (1997) characterized the presence of a β-1,2-mannosyltransferase in *Candida guilliermondii*, however, a gene for this enzyme has yet to be cloned.

In *C. albicans* yeast, both the β-oligomannosides which make up the acid-labile region of the phosphomannan complex, and α-oligomannosides, which make up the acid-stable region of the complex, serve as adhesins in the attachment of these pathogenic yeast cells to host splenic and lymph node macrophages (Cutler, 2001). Interestingly, antibodies protective against various forms of candidiasis recognize β-linked mannotriose, but not oligomannosides of greater mannose chain length (Han et al, 1997). It was reported that patients who develop deep tissue invasion with *C. albicans*, do not have detectable antibody titers specific for β-linked oligomannosides, whereas such antibodies were present in healthy individuals (Jouault et al, 1997).

There are few examples of β-linked mannose residues on glycoproteins from *P. pastoris*. In 1986, Kobayashi et al, described a modified acetolysis method with milder conditions for the isolation of manno-oligosaccharides composed predominantly of β-1,2 linked mannose residues. In 2003, Trimble et al reported the presence of β-1,2-linked mannose residues in the recombinant human bile salt-stimulated lipase (hBSSL) expressed in *P. pastoris*. As evidenced by the presence of protective antibodies in uninfected individuals, β-linked mannans are likely to be immunogenic. Additionally, exposed mannose groups on therapeutic proteins are rapidly cleared by mannose receptors on macrophage cells, resulting in low drug efficacy. Thus, the presence of β-linked mannose residues on N- or O-linked glycans of heterologous therapeutic proteins expressed in a fungal host e.g., *P. pastoris* is not desirable given their immunogenic potential and their ability to bind to clearance factors.

What is needed, therefore, is a method for removing undesired mannose residues on glycoproteins for the production of therapeutic glycoproteins.

SUMMARY OF INVENTION

Accordingly, the present invention provides methods for producing glycoprotein compositions in yeast or filamentous fungal host cells, said glycoprotein compositions having reduced amounts of high mannose glycans, said method comprising reducing or eliminating the presence of α-mannosidase resistant glycans on said glycoproteins. In certain embodiments, reducing or eliminating α-mannosidase resistant glycans on glycoproteins is accomplished by modifying the host cell through disruption, deletion or mutation of a gene involved in mannosylation of N-glycans. Such genes may include, for example, the gene sequences described herein as SEQ ID NO:11, or variants thereof.

In certain embodiments, the α-mannosidase resistant glycans may comprise β-mannose, branched high mannose, or α-1,4 mannose residues.

The host cells of the present invention are preferably of yeast and/or filamentous fungal origin. The host cells useful in the present invention may include the following families, genie, and species: *Pichia pastoris, Pichia finlandica, Pichia trehalophila, Pichia koclamae, Pichia membranaefaciens, Pichia methanolica, Pichia minuta (Ogataea minuta, Pichia lindneri), Pichia opuntiae, Pichia thermotolerans, Pichi salictaria, Pichia guercum, Pichia pijperi, Pichia stiptis, Pichia sp., Saccharomyces castelii, Saccharomyces cerevisiae, Saccharomyces kluyveri, Saccharomyces sp., Hansenula polymorpha, Kluyveromyces sp., Kluyveromyces lactis, Candida albicans, Candida sp., Aspergillus fumigatus, Aspergillus nidulans, Aspergillus niger, Aspergillus oryzae, Trichoderma reesei, Chrysosporium lucknowense, Fusarium sp., Fusarium gramineum, Fusarium venenatum, Physcomitrella patens* and *Neurospora crassa*.

In certain embodiments, the host cells of the present invention may comprise a deletion of a functional gene encoding an alpha-1,6-mannosyltransferase activity, such as OCH1. In other embodiments, the host cells of the present invention may further comprise a gene encoding an mannosylphosphate transferase activity, such as PNO1 and MNN4B.

The present invention also provides glycoprotein compositions with reduced amounts of high mannose glycan structures that are recalcitrant to α-mannosidase, which may be produced by the methods of the present invention. Such glycoprotein compositions may comprise either N-linked glycans and/or O-linked glycans.

The present invention further provides isolated nucleic acid sequences which are involved in the production of α-mannosidase resistant glycans. These isolated nucleic acid sequences include the sequences described herein as SEQ ID NO:11,or variants thereof. Also included in the present invention are other nucleic acid sequences which exhibit structural similarity to the above sequences. These may include, for example, degenerate variants of SEQ ID NO:11, as well as nucleic acid sequences having a high level of nucleotide sequence identity with the above. Nucleic acid sequences included in the present invention would therefore include those nucleic acid sequences having at least 72% 75%, 80% or 85% 90%, 95%, 98%, 99%, 99.9% identity to the sequences of SEQ ID NO:11, as well as nucleic acid sequences that encode a polypeptide having the amino acid sequences which is produced by SEQ ID NO:11, nucleic acid sequence that encode polypeptides having at least 72% 75%, 80% or 85% 90%, 95%, 98%, 99%, 99.9% identity to the polypeptides having the amino acid sequences which are produced by SEQ ID NO:12, SEQ ID NO:13, SEQ ID NO:14, SEQ ID NO:15; and nucleic acid sequences that hybridize under stringent conditions to the nucleic acid sequences described as SEQ ID NO:11, The present invention also includes nucleic acid sequences comprising a fragment of any of the above nucleic acid sequences that is at least 60 contiguous nucleotides in length.

In still other embodiments, the present invention provides modified yeast or filamentous fungal host cells. The host cells of the present invention may be characterized as having been modified to reduce expression of the functional gene products of one or more a nucleic acid sequence selected from the group consisting of SEQ ID NO:11. In certain embodiments, the modified host cell comprises a disruption, deletion or mutation in one or more nucleic acid sequences selected from the group consisting of SEQ ID NO:11. In other embodiments, the modified host cell comprises a cellular inhibitor of expression of the functional gene product of a nucleic acid selected from the group consisting of SEQ ID NO:11, or variants thereof. Cellular inhibitors of expression useful for the present invention include, for example antisense DNA and short interfering RNA.

In other embodiments, the present invention may comprise modified yeast or filamentous fungal host cells which are capable of expressing glycoprotein compositions having reduced amounts of high mannose glycans, said glycoprotein compositions comprising reduced presence of α-mannosidase resistant glycans, for example β-mannosyl residues.

BRIEF DESCRIPTION OF THE DRAWINGS

FIG. 1 depicts the nucleic acid (SEQ ID NO:11) and amino acid sequence (SEQ ID NO:12) of the *P. pastoris* AMR2 gene.

Figure 5A:
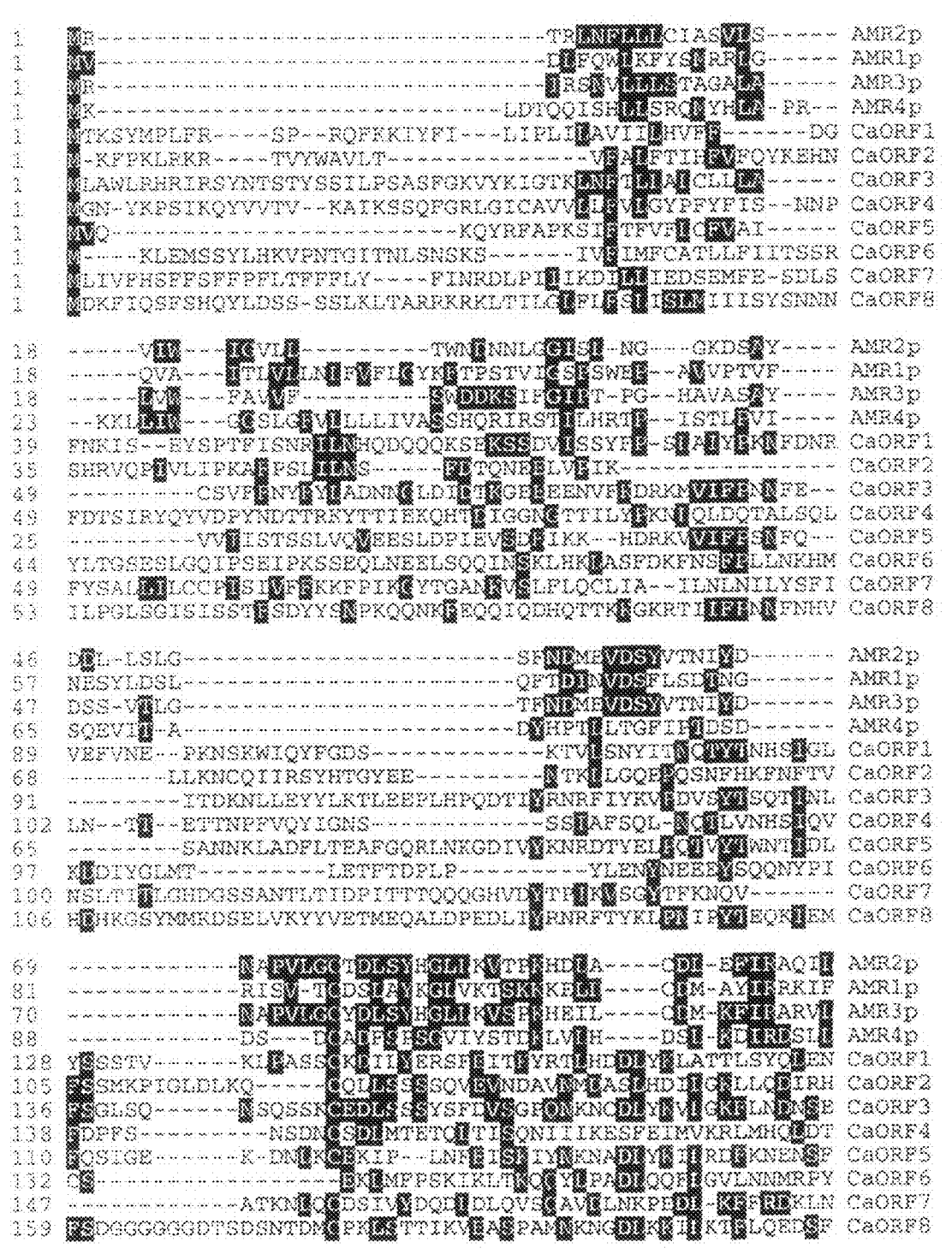
Figure 5B:
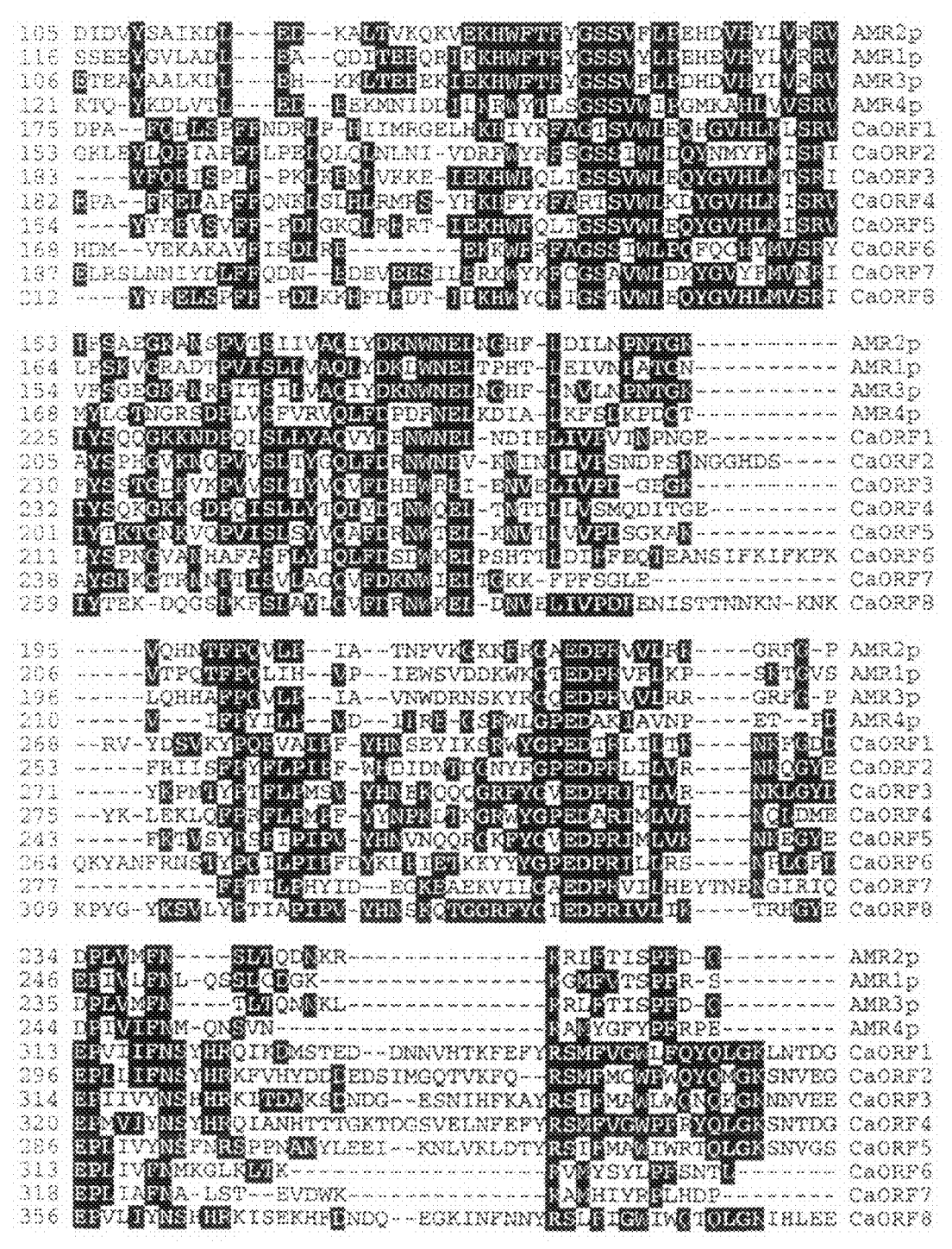
Figure 5C:
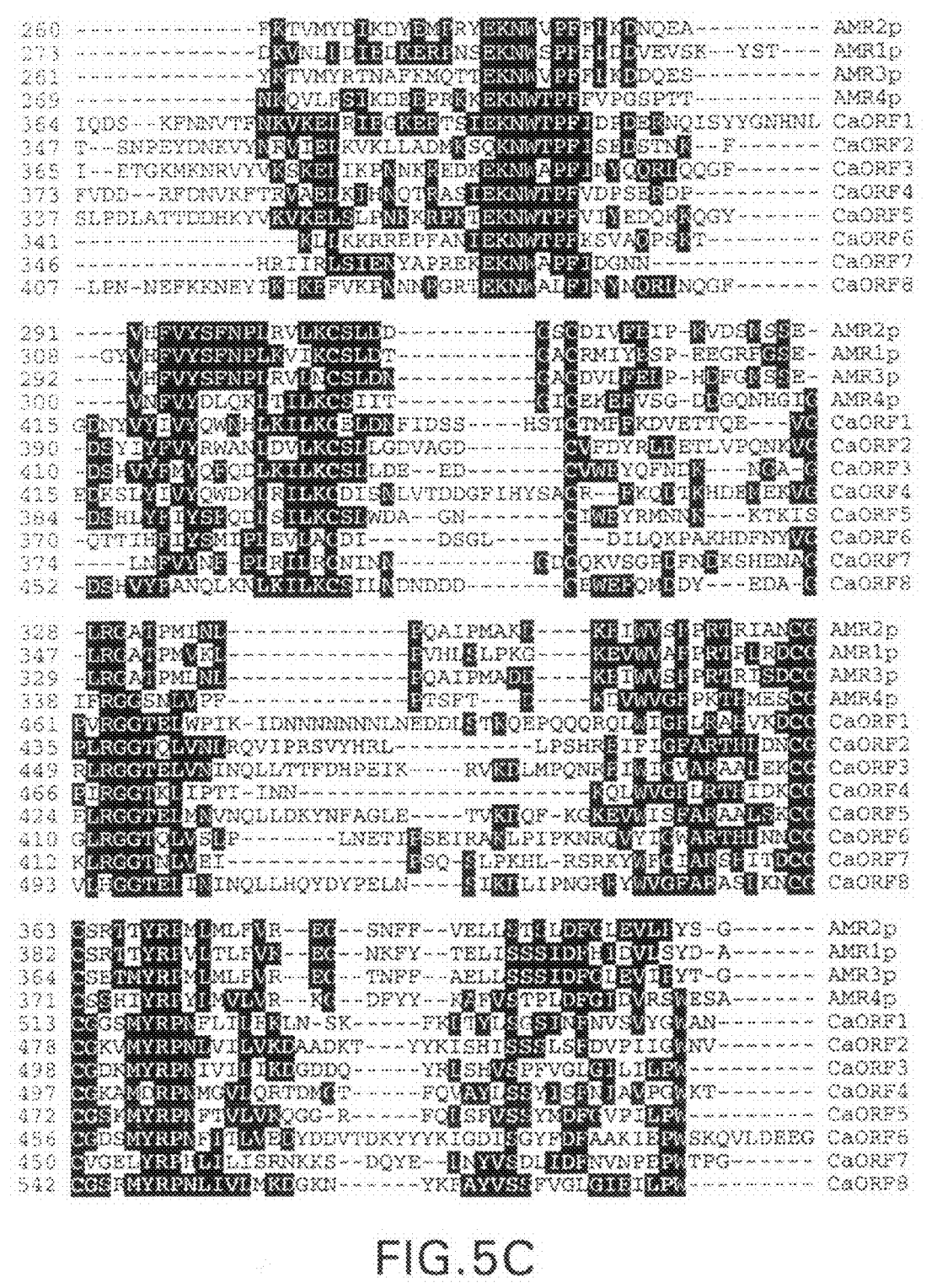
Figure 5D:
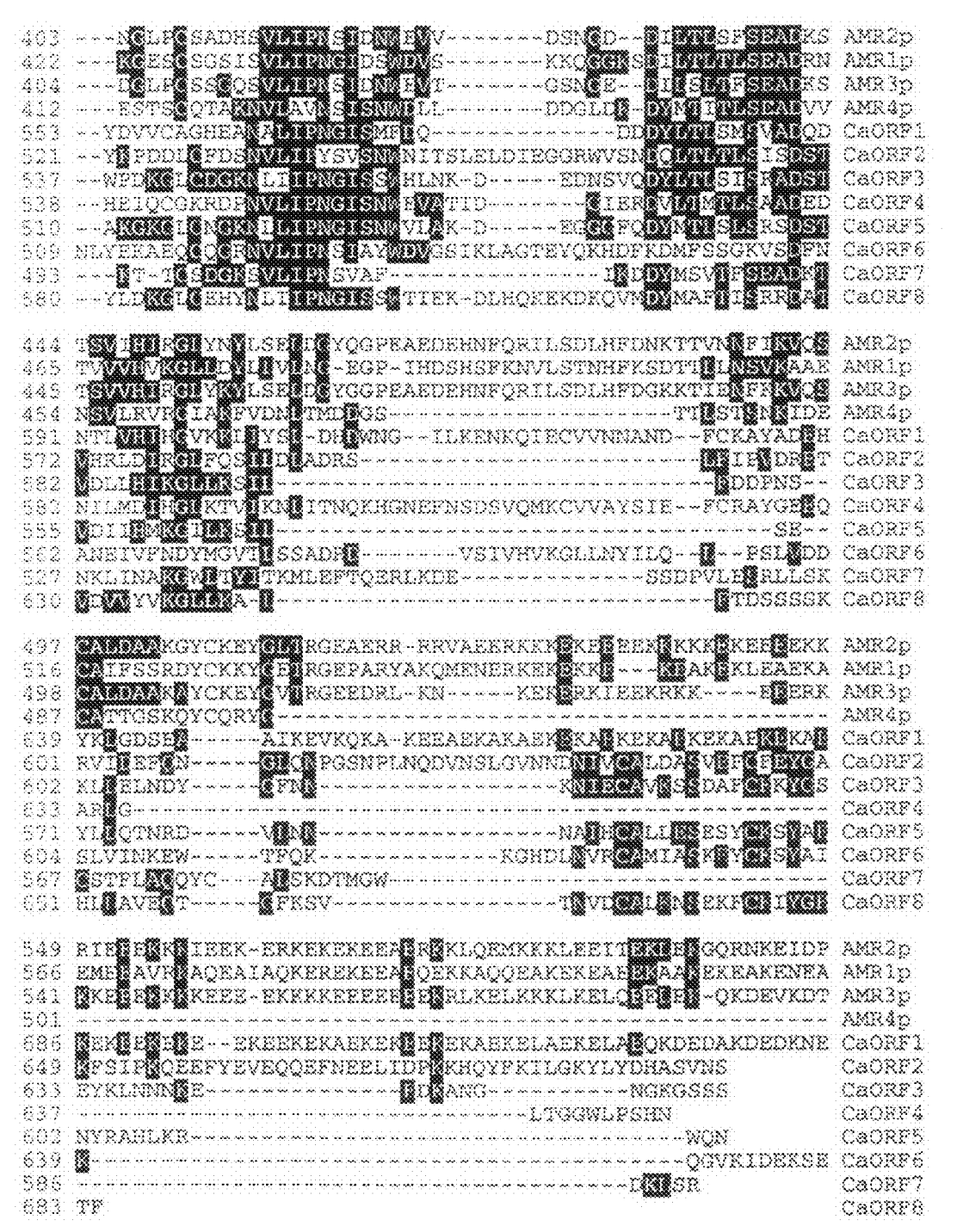

FIG. 5 The deduced amino acid sequence of the *P. pastoris* AMR2 gene is shown aligned with the amino acid sequence of AMR2 homologs from *Candida albicans*. AMR2p (SEQ ID NO:12), AMR1p (SEQ ID NO:13). AMR3p (SEQ ID NO:14) AMR4p (SEQ ID NO:15), CaORF1 (SEQ ID NO:16), CaORF2 (SEQ ID NO:17). CaORF3 (SEQ ID NO:18), CaORF4 (SEQ ID NO:19), CaORF5 (SEQ ID NO:20), CaORF6 (SEQ ID NO:21), CaORF7 (SEQ ID NO:22), CaORF8 (SEQ ID NO:23).

DETAILED DESCRIPTION OF THE INVENTION

Figure 2D:
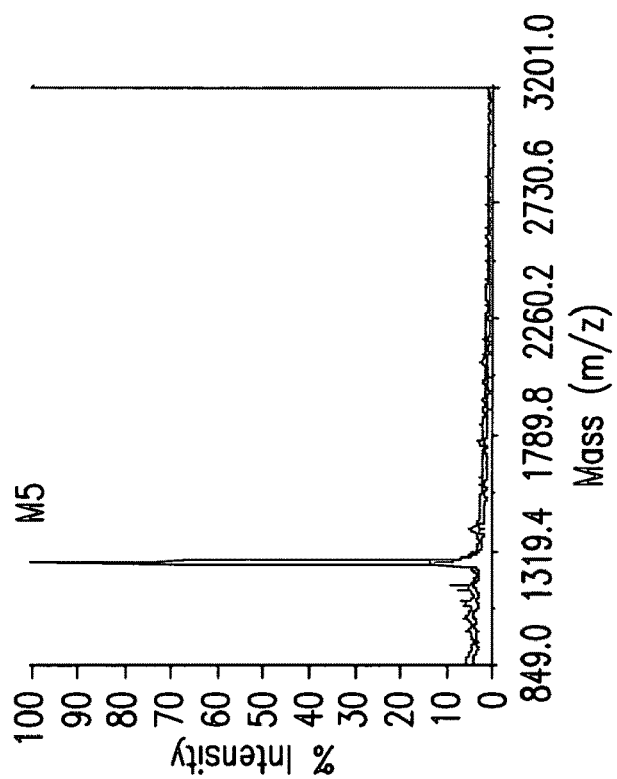
FIG. 2 A. MALDI-TOF MS showing the N-glycans of *P. pastoris* YAS137 (Δoch1, Δpno1, Δmnn4b). B. MALDI-TOF MS showing the N-glycans of *P. pastoris* YAS137 after digestion with α-1,2 mannosidase. C. MALDI-TOF MS showing the N-glycans of *P. pastoris* PBP130 (Δoch1, Δpno1, Δmnn4b, Δamr2). D. MALDI-TOF MS showing the N-glycans of *P. pastoris* PBP130 (Δoch1, Δpno1, Δmnn4b, Δamr2) after digestion with α-1,2 mannosidase.
Figure 2C:
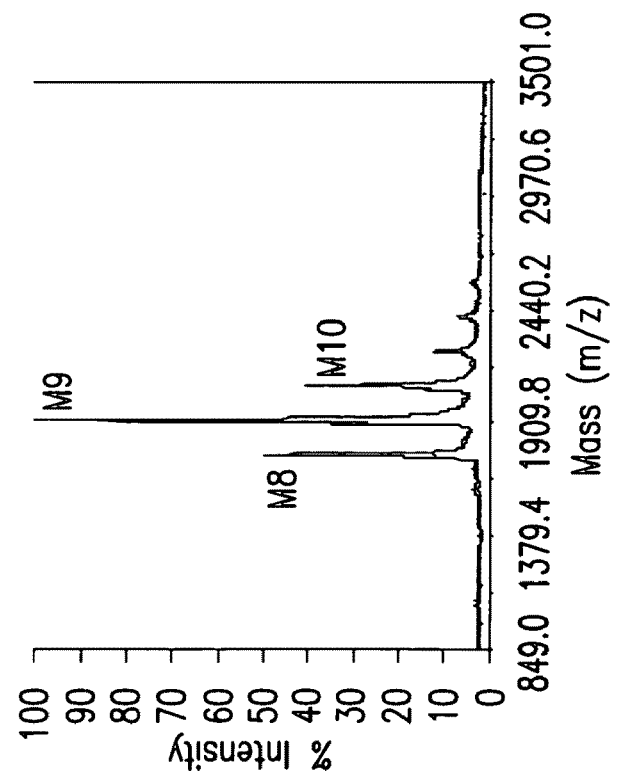

Unless otherwise defined herein, scientific and technical terms used in connection with the present invention shall have the meanings that are commonly understood by those of ordinary skill in the art. Further, unless otherwise required by context, singular terms shall include the plural and plural terms shall include the singular. Generally, nomenclatures used in connection with, and techniques of biochemistry, enzymology, molecular and cellular biology, microbiology, genetics and protein and nucleic acid chemistry and hybridization described herein are those well known and commonly used in the art. The methods and techniques of the present invention are generally performed according to conventional methods well known in the art and as described in various general and more specific references that are cited and discussed throughout the present specification unless otherwise indicated. See, e.g., Sambrook et al. *Molecular Cloning: A Laboratory Manual*, 2d ed., Cold Spring Harbor Laboratory Press, Cold Spring Harbor, N.Y. (1989); Ausubel et al., *Current Protocols in Molecular Biology*, Greene Publishing Associates (1992, and Supplements to 2002); Harlow and Lane, *Antibodies: A Laboratory Manual*, Cold Spring Harbor Laboratory Press, Cold Spring Harbor, N.Y. (1990); Taylor and Drickamer, *Introduction to Glycobiology*, Oxford Univ. Press (2003); *Worthington Enzyme Manual*, Worthington Biochemical Corp., Freehold, N.J.; *Handbook of Biochemistry: Section A Proteins*, Vol I, CRC Press (1976); *Handbook of Biochemistry: Section A Proteins*, Vol II, CRC Press (1976); *Essentials of Glycobiology*, Cold Spring Harbor Laboratory Press (1999).

All publications, patents and other references mentioned herein are hereby incorporated by reference in their entireties.

The following terms, unless otherwise indicated, shall be understood to have the following meanings:

The term "polynucleotide" or "nucleic acid molecule" refers to a polymeric form of nucleotides of at least 10 bases in length. The term includes DNA molecules (e.g., cDNA or genomic or synthetic DNA) and RNA molecules (e.g., mRNA or synthetic RNA), as well as analogs of DNA or RNA containing non-natural nucleotide analogs, non-native internucleoside bonds, or both. The nucleic acid can be in any topological conformation. For instance, the nucleic acid can be single-stranded, double-stranded, triple-stranded, quadruplexed, partially double-stranded, branched, hairpinned, circular, or in a padlocked conformation.

Unless otherwise indicated, a "nucleic acid comprising SEQ ID NO:X" refers to a nucleic acid, at least a portion of which has either (i) the sequence of SEQ ID NO:X, or (ii) a sequence complementary to SEQ ID NO:X. The choice between the two is dictated by the context. For instance, if the nucleic acid is used as a probe, the choice between the two is dictated by the requirement that the probe be complementary to the desired target.

An "isolated" or "substantially pure" nucleic acid or polynucleotide (e.g., an RNA, DNA or a mixed polymer) is one which is substantially separated from other cellular components that naturally accompany the native polynucleotide in its natural host cell, e.g., ribosomes, polymerases and genomic sequences with which it is naturally associated. The term embraces a nucleic acid or polynucleotide that (1) has been removed from its naturally occurring environment, (2) is not associated with all or a portion of a polynucleotide in which the "isolated polynucleotide" is found in nature, (3) is operatively linked to a polynucleotide which it is not linked to in nature, or (4) does not occur in nature. The term "isolated" or "substantially pure" also can be used in reference to recombinant or cloned DNA isolates, chemically synthesized polynucleotide analogs, or polynucleotide analogs that are biologically synthesized by heterologous systems.

However, "isolated" does not necessarily require that the nucleic acid or polynucleotide so described has itself been physically removed from its native environment. For instance, an endogenous nucleic acid sequence in the genome of an organism is deemed "isolated" herein if a heterologous sequence is placed adjacent to the endogenous nucleic acid sequence, such that the expression of this endogenous nucleic acid sequence is altered. In this context, a heterologous sequence is a sequence that is not naturally adjacent to the endogenous nucleic acid sequence, whether or not the heterologous sequence is itself endogenous (originating from the same host cell or progeny thereof) or exogenous (originating from a different host cell or progeny thereof). By way of example, a promoter sequence can be substituted (e.g., by homologous recombination) for the native promoter of a gene in the genome of a host cell, such that this gene has an altered expression pattern. This gene would now become "isolated" because it is separated from at least some of the sequences that naturally flank it.

A nucleic acid is also considered "isolated" if it contains any modifications that do not naturally occur to the corresponding nucleic acid in a genome. For instance, an endogenous coding sequence is considered "isolated" if it contains an insertion, deletion or a point mutation introduced artificially, e.g., by human intervention. An "isolated nucleic acid" also includes a nucleic acid integrated into a host cell chromosome at a heterologous site and a nucleic acid construct present as an episome. Moreover, an "isolated nucleic acid" can be substantially free of other cellular material, or substantially free of culture medium when produced by recombinant techniques, or substantially free of chemical precursors or other chemicals when chemically synthesized.

As used herein, the phrase "degenerate variant" of a reference nucleic acid sequence encompasses nucleic acid sequences that can be translated, according to the standard genetic code, to provide an amino acid sequence identical to that translated from the reference nucleic acid sequence. The term "degenerate oligonucleotide" or "degenerate primer" is used to signify an oligonucleotide capable of hybridizing with target nucleic acid sequences that are not necessarily identical in sequence but that are homologous to one another within one or more particular segments.

The term "percent sequence identity" or "identical" in the context of nucleic acid sequences refers to the residues in the two sequences which are the same when aligned for maximum correspondence. The length of sequence identity comparison may be over a stretch of at least about nine nucleotides, usually at least about 20 nucleotides, more usually at least about 24 nucleotides, typically at least about 28 nucleotides, more typically at least about 32 nucleotides, and preferably at least about 36 or more nucleotides. There are a number of different algorithms known in the art which can be used to measure nucleotide sequence identity. For instance, polynucleotide sequences can be compared using FASTA, Gap or Bestfit, which are programs in Wisconsin Package Version 10.0, Genetics Computer Group (GCG), Madison, Wis. FASTA provides alignments and percent sequence identity of the regions of the best overlap between the query and search sequences. Pearson, *Methods Enzymol.* 183:63-98 (1990) (hereby incorporated by reference in its entirety). For instance, percent sequence identity between nucleic acid sequences can be determined using FASTA with its default parameters (a word size of 6 and the NOPAM factor for the scoring matrix) or using Gap with its default parameters as provided in GCG Version 6.1, herein incorporated by reference. Alternatively, sequences can be compared using the computer program, BLAST (Altschul et al., *J. Mol. Biol.* 215:403-410 (1990); Gish and States, *Nature Genet.* 3:266-272 (1993); Madden et al., *Meth. Enzymol.* 266:131-141 (1996); Altschul et al., *Nucleic Acids Res.* 25:3389-3402 (1997); Zhang and Madden, *Genome Res.* 7:649-656 (1997)), especially blastp or tblastn (Altschul et al., *Nucleic Acids Res.* 25:3389-3402 (1997)).

The term "substantial homology" or "substantial similarity," when referring to a nucleic acid or fragment thereof, indicates that, when optimally aligned with appropriate nucleotide insertions or deletions with another nucleic acid (or its complementary strand), there is nucleotide sequence identity in at least about 50%, more preferably 60% of the nucleotide bases, usually at least about 70%, more usually at least about 80%, preferably at least about 90%, and more preferably at least about 95%, 96%, 97%, 98% or 99% of the nucleotide bases, as measured by any well-known algorithm of sequence identity, such as FASTA, BLAST or Gap, as discussed above.

Alternatively, substantial homology or similarity exists when a nucleic acid or fragment thereof hybridizes to another nucleic acid, to a strand of another nucleic acid, or to the complementary strand thereof, under stringent hybridization conditions. "Stringent hybridization conditions" and "stringent wash conditions" in the context of nucleic acid hybridization experiments depend upon a number of different physical parameters. Nucleic acid hybridization will be affected by such conditions as salt concentration, temperature, solvents, the base composition of the hybridizing species, length of the complementary regions, and the number of nucleotide base mismatches between the hybridizing nucleic acids, as will be readily appreciated by those skilled in the art. One having ordinary skill in the art knows how to vary these parameters to achieve a particular stringency of hybridization.

In general, "stringent hybridization" is performed at about 25° C. below the thermal melting point ($T_m$) for the specific DNA hybrid under a particular set of conditions. "Stringent washing" is performed at temperatures about 5° C. lower than the $T_m$ for the specific DNA hybrid under a particular set of conditions. The $T_m$ is the temperature at which 50% of the target sequence hybridizes to a perfectly matched probe. See Sambrook et al., *Molecular Cloning: A Laboratory Manual*, 2d ed., Cold Spring Harbor Laboratory Press, Cold Spring Harbor, N.Y. (1989), page 9.51, hereby incorporated by reference. For purposes herein, "stringent conditions" are defined for solution phase hybridization as aqueous hybridization (i.e., free of formamide) in 6×SSC (where 20×SSC contains 3.0 M NaCl and 0.3 M sodium citrate), 1% SDS at 65° C. for 8-12 hours, followed by two washes in 0.2×SSC, 0.1% SDS at 65° C. for 20 minutes. It will be appreciated by the skilled worker that hybridization at 65° C. will occur at different rates depending on a number of factors including the length and percent identity of the sequences which are hybridizing.

The nucleic acids (also referred to as polynucleotides) of this invention may include both sense and antisense strands of RNA, cDNA, genomic DNA, and synthetic forms and mixed polymers of the above. They may be modified chemically or biochemically or may contain non-natural or derivatized nucleotide bases, as will be readily appreciated by those of skill in the art. Such modifications include, for example, labels, methylation, substitution of one or more of the naturally occurring nucleotides with an analog, internucleotide modifications such as uncharged linkages (e.g., methyl phosphonates, phosphotriesters, phosphoramidates, carbamates, etc.), charged linkages (e.g., phosphorothioates, phosphorodithioates, etc.), pendent moieties (e.g., polypeptides), intercalators (e.g., acridine, psoralen, etc.), chelators, alkylators, and modified linkages (e.g., alpha anomeric nucleic acids, etc.) Also included are synthetic molecules that mimic polynucleotides in their ability to bind to a designated sequence via hydrogen bonding and other chemical interactions. Such molecules are known in the art and include, for example, those in which peptide linkages substitute for phosphate linkages in the backbone of the molecule. Other modifications can include, for example, analogs in which the ribose ring contains a bridging moiety or other structure such as the modifications found in "locked" nucleic acids.

The term "mutated" when applied to nucleic acid sequences means that nucleotides in a nucleic acid sequence may be inserted, deleted or changed compared to a reference nucleic acid sequence. A single alteration may be made at a locus (a point mutation) or multiple nucleotides may be inserted, deleted or changed at a single locus. In addition, one or more alterations may be made at any number of loci within a nucleic acid sequence. A nucleic acid sequence may be mutated by any method known in the art including but not limited to mutagenesis techniques such as "error-prone PCR" (a process for performing PCR under conditions where the copying fidelity of the DNA polymerase is low, such that a high rate of point mutations is obtained along the entire length of the PCR product; see, e.g., Leung et al., *Technique*, 1:11-15 (1989) and Caldwell and Joyce, *PCR Methods Applic.* 2:28-33 (1992)); and "oligonucleotide-directed mutagenesis" (a process which enables the generation of site-specific mutations in any cloned DNA segment of interest; see, e.g., Reidhaar-Olson and Sauer, *Science* 241:53-57 (1988)).

The term "vector" as used herein is intended to refer to a nucleic acid molecule capable of transporting another nucleic acid to which it has been linked. One type of vector is a "plasmid", which refers to a circular double stranded DNA loop into which additional DNA segments may be ligated. Other vectors include cosmids, bacterial artificial chromosomes (BAC) and yeast artificial chromosomes (YAC). Another type of vector is a viral vector, wherein additional DNA segments may be ligated into the viral genome (discussed in more detail below). Certain vectors are capable of autonomous replication in a host cell into which they are introduced (e.g., vectors having an origin of replication which functions in the host cell). Other vectors can be integrated into the genome of a host cell upon introduction into the host cell, and are thereby replicated along with the host genome. Moreover, certain preferred vectors are capable of directing the expression of genes to which they are operatively linked. Such vectors are referred to herein as "recombinant expression vectors" (or simply, "expression vectors").

As used herein, the term "sequence of interest" or "gene of interest" refers to a nucleic acid sequence, typically encoding a protein that is not normally produced in the host cell. The methods disclosed herein allow one or more sequences of interest or genes of interest to be integrated into a host cell genome. A preferred integration site is the AMR2 locus. Non-limiting examples of sequences of interest include sequences encoding one or more polypeptides having an enzymatic activity, e.g., an enzyme which affects N-glycan synthesis in a host such as mannosyltransferases, N-acetylglucosaminyltransferases, UDP-N-acetylglucosamine transporters, galactosyltransferases and sialyltransferases.

As used herein, the term "therapeutic glycoprotein" includes erythropoietin, cytokines such as interferon-$\alpha$, interferon-$\beta$, interferon-$\gamma$, interferon-$\omega$, and granulocyte-CSF, GM-CSF, coagulation factors such as factor VIII, factor IX, and human protein C, antithrombin III, thrombin, soluble IgE receptor $\alpha$-chain, IgG, IgG fragments, IgG fusions, IgM, interleukins, urokinase, chymase, and urea trypsin inhibitor, IGF-binding protein, epidermal growth factor, growth hormone-releasing factor, annexin V fusion protein, angiostatin, vascular endothelial growth factor-2, myeloid progenitor inhibitory factor-1, osteoprotegerin, $\alpha$-1-antitrypsin, $\alpha$-feto proteins, DNase II, kringle 3 of human plasminogen, glucocerebrosidase, TNF binding protein 1, follicle stimulating hormone, cytotoxic T lymphocyte associated antigen 4-Ig, transmembrane activator and calcium modulator and cyclophilin ligand, soluble TNF receptor Fc fusion, glucagon-like protein 1, IL-2 receptor agonist.

"Operatively linked" expression control sequences refers to a linkage in which the expression control sequence is contiguous with the gene of interest to control the gene of interest, as well as expression control sequences that act in trans or at a distance to control the gene of interest.

The term "expression control sequence" as used herein refers to polynucleotide sequences which are necessary to affect the expression of coding sequences to which they are operatively linked. Expression control sequences are sequences which control the transcription, post-transcriptional events and translation of nucleic acid sequences. Expression control sequences include appropriate transcription initiation, termination, promoter and enhancer sequences; efficient RNA processing signals such as splicing and polyadenylation signals; sequences that stabilize cytoplasmic mRNA; sequences that enhance translation efficiency (e.g., ribosome binding sites); sequences that enhance protein stability; and when desired, sequences that enhance protein secretion. The nature of such control sequences differs depending upon the host organism; in prokaryotes, such control sequences generally include promoter, ribosomal binding site, and transcription termination sequence. The term "control sequences" is intended to include, at a minimum, all components whose presence is essential for expression, and can also include additional components whose presence is advantageous, for example, leader sequences and fusion partner sequences.

The term "recombinant host cell" (or simply "host cell"), as used herein, is intended to refer to a cell into which a recombinant vector has been introduced. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein. A recombinant host cell may be an isolated cell or cell line grown in culture or may be a cell which resides in a living tissue or organism.

The term "peptide" as used herein refers to a short polypeptide, e.g., one that is typically less than about 50 amino acids long and more typically less than about 30 amino acids long. The term as used herein encompasses analogs and mimetics that mimic structural and thus biological function.

The term "polypeptide" encompasses both naturally-occurring and non-naturally-occurring proteins, and fragments, mutants, derivatives and analogs thereof. A polypeptide may be monomeric or polymeric; Further, a polypeptide may comprise a number of different domains each of which has one or more distinct activities.

The term "isolated protein" or "isolated polypeptide" is a protein or polypeptide that by virtue of its origin or source of derivation (1) is not associated with naturally associated components that accompany it in its native state, (2) exists in a purity not found in nature, where purity can be adjudged with respect to the presence of other cellular material (e.g., is free of other proteins from the same species) (3) is expressed by a cell from a different species, or (4) does not occur in nature (e.g., it is a fragment of a polypeptide found in nature or it includes amino acid analogs or derivatives not found in nature or linkages other than standard peptide bonds). Thus, a polypeptide that is chemically synthesized or synthesized in a cellular system different from the cell from which it naturally originates will be "isolated" from its naturally associated components. A polypeptide or protein may also be rendered substantially free of naturally associated components by isolation, using protein purification techniques well known in the art. As thus defined, "isolated" does not necessarily require that the protein, polypeptide, peptide or oligopeptide so described has been physically removed from its native environment.

The term "polypeptide fragment" as used herein refers to a polypeptide that has a deletion, e.g., an amino-terminal and/or carboxy-terminal deletion compared to a full-length polypeptide. In a preferred embodiment, the polypeptide fragment is a contiguous sequence in which the amino acid sequence of the fragment is identical to the corresponding positions in the naturally-occurring sequence. Fragments typically are at least 5, 6, 7, 8, 9 or 10 amino acids long, preferably at least 12, 14, 16 or 18 amino acids long, more preferably at least 20 amino acids long, more preferably at least 25, 30, 35, 40 or 45, amino acids, even more preferably at least 50 or 60 amino acids long, and even more preferably at least 70 amino acids long.

A "modified derivative" refers to polypeptides or fragments thereof that are substantially homologous in primary structural sequence but which include, e.g., in vivo or in vitro chemical and biochemical modifications or which incorporate amino acids that are not found in the native polypeptide. Such modifications include, for example, acetylation, carboxylation, phosphorylation, glycosylation, ubiquitination, labeling, e.g., with radionuclides, and various enzymatic modifications, as will be readily appreciated by those skilled in the art. A variety of methods for labeling polypeptides and of substituents or labels useful for such purposes are well known in the art, and include radioactive isotopes such as $^{125}$I, $^{32}$P, $^{35}$S, and $^3$H, ligands which bind to labeled antiligands (e.g., antibodies), fluorophores, chemiluminescent agents, enzymes, and antiligands which can serve as specific binding pair members for a labeled ligand. The choice of label depends on the sensitivity required, ease of conjugation with the primer, stability requirements, and available instrumentation. Methods for labeling polypeptides are well known in the art. See, e.g., Ausubel et al., *Current Protocols in Molecular Biology*, Greene Publishing Associates (1992, and Supplements to 2002) (hereby incorporated by reference).

The term "fusion protein" refers to a polypeptide comprising a polypeptide or fragment coupled to heterologous amino acid sequences. Fusion proteins are useful because they can be constructed to contain two or more desired functional elements from two or more different proteins. A fusion protein comprises at least 10 contiguous amino acids from a polypeptide of interest, more preferably at least 20 or 30 amino acids, even more preferably at least 40, 50 or 60 amino acids, yet more preferably at least 75, 100 or 125 amino acids. Fusions that include the entirety of the proteins of the present invention have particular utility. The heterologous polypeptide included within the fusion protein of the present invention is at least 6 amino acids in length, often at least 8 amino acids in length, and usefully at least 15, 20, and 25 amino acids in length. Fusions that include larger polypeptides, such as an IgG Fc region, and even entire proteins, such as the green fluorescent protein ("GFP") chromophore-containing proteins, have particular utility. Fusion proteins can be produced recombinantly by constructing a nucleic acid sequence which encodes the polypeptide or a fragment thereof in frame with a nucleic acid sequence encoding a different protein or peptide and then expressing the fusion protein. Alternatively, a fusion protein can be produced chemically by crosslinking the polypeptide or a fragment thereof to another protein.

As used herein, the term "antibody" refers to a polypeptide, at least a portion of which is encoded by at least one immunoglobulin gene, or fragment thereof, and that can bind specifically to a desired target molecule. The term includes naturally-occurring forms, as well as fragments and derivatives.

Fragments within the scope of the term "antibody" include those produced by digestion with various proteases, those produced by chemical cleavage and/or chemical dissociation and those produced recombinantly, so long as the fragment remains capable of specific binding to a target molecule. Among such fragments are Fab, Fab', Fv, F(ab')$_2$, and single chain Fv (scFv) fragments.

Derivatives within the scope of the term include antibodies (or fragments thereof) that have been modified in sequence, but remain capable of specific binding to a target molecule, including: interspecies chimeric and humanized antibodies; antibody fusions; heteromeric antibody complexes and antibody fusions, such as diabodies (bispecific antibodies), single-chain diabodies, and intrabodies (see, e.g., *Intracellular Antibodies: Research and Disease Applications*, (Marasco, ed., Springer-Verlag New York, Inc., 1998), the disclosure of which is incorporated herein by reference in its entirety).

As used herein, antibodies can be produced by any known technique, including harvest from cell culture of native B lymphocytes, harvest from culture of hybridomas, recombinant expression systems and phage display.

The term "non-peptide analog" refers to a compound with properties that are analogous to those of a reference polypeptide. A non-peptide compound may also be termed a "peptide mimetic" or a "peptidomimetic". See, e.g., Jones, *Amino Acid and Peptide Synthesis*, Oxford University Press (1992); Jung, *Combinatorial Peptide and Nonpeptide Libraries: A Handbook*, John Wiley (1997); Bodanszky et al., *Peptide Chemistry—A Practical Textbook*, Springer Verlag (1993); *Synthetic Peptides: A Users Guide*, (Grant, ed., W. H. Freeman and Co., 1992); Evans et al., *J. Med. Chem.* 30:1229 (1987); Fauchere, *J. Adv. Drug Res.* 15:29 (1986); Veber and Freidinger, *Trends Neurosci.*, 8:392-396 (1985); and references sited in each of the above, which are incorporated herein by reference. Such compounds are often developed with the aid of computerized molecular modeling. Peptide mimetics that are structurally similar to useful peptides of the invention may be used to produce an equivalent effect and are therefore envisioned to be part of the invention.

A "polypeptide mutant" or "mutein" refers to a polypeptide whose sequence contains an insertion, duplication, deletion, rearrangement or substitution of one or more amino acids compared to the amino acid sequence of a native or wild-type protein. A mutein may have one or more amino acid point substitutions, in which a single amino acid at a position has been changed to another amino acid, one or more insertions and/or deletions, in which one or more amino acids are inserted or deleted, respectively, in the sequence of the naturally-occurring protein, and/or truncations of the amino acid sequence at either or both the amino or carboxy termini. A mutein may have the same but preferably has a different biological activity compared to the naturally-occurring protein.

A mutein has at least 65% overall sequence homology to its wild-type counterpart. Even more preferred are muteins having at least 70%, 75%, 80%, 85% or 90% overall sequence homology to the wild-type protein. In an even more preferred embodiment, a mutein exhibits at least 95% sequence identity, even more preferably 98%, even more preferably 99% and even more preferably 99.9% overall sequence identity. Sequence homology may be measured by any common sequence analysis algorithm, such as Gap or Bestfit.

Amino acid substitutions can include those which: (1) reduce susceptibility to proteolysis, (2) reduce susceptibility to oxidation, (3) alter binding affinity for forming protein complexes, (4) alter binding affinity or enzymatic activity, and (5) confer or modify other physicochemical or functional properties of such analogs.

As used herein, the twenty conventional amino acids and their abbreviations follow conventional usage. See *Immunology—A Synthesis* (Golub and Gren eds., Sinauer Associates, Sunderland, Mass., 2$^{nd}$ ed. 1991), which is incorporated herein by reference. Stereoisomers (e.g., D-amino acids) of the twenty conventional amino acids, unnatural amino acids such as α-, α-disubstituted amino acids, N-alkyl amino acids, and other unconventional amino acids may also be suitable components for polypeptides of the present invention. Examples of unconventional amino acids include: 4-hydroxyproline, γ-carboxyglutamate, ϵ-N,N,N-trimethyllysine, ϵ-N-acetyllysine, O-phosphoserine, N-acetylserine, N-formylmethionine, 3-methylhistidine, 5-hydroxylysine, N-methylarginine, and other similar amino acids and imino acids (e.g., 4-hydroxyproline). In the polypeptide notation used herein, the left-hand end corresponds to the amino terminal end and the right-hand end corresponds to the carboxy-terminal end, in accordance with standard usage and convention.

A protein has "homology" or is "homologous" to a second protein if the nucleic acid sequence that encodes the protein has a similar sequence to the nucleic acid sequence that encodes the second protein. Alternatively, a protein has homology to a second protein if the two proteins have "similar" amino acid sequences. (Thus, the term "homologous proteins" is defined to mean that the two proteins have similar amino acid sequences.) In a preferred embodiment, a homologous protein is one that exhibits at least 72% sequence homology to the wild type protein, more preferred is at least 75% sequence homology.

Even more preferred are homologous proteins that exhibit at least 80%, 85%, 90% or 95% sequence homology to the wild type protein. In a yet more preferred embodiment, a homologous protein exhibits at least 96%, 98%, 99% or 99.9% sequence identity. As used herein, homology between two regions of amino acid sequence (especially with respect to predicted structural similarities) is interpreted as implying similarity in function.

When "homologous" is used in reference to proteins or peptides, it is recognized that residue positions that are not identical often differ by conservative amino acid substitutions. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. In cases where two or more amino acid sequences differ from each other by conservative substitutions, the percent sequence identity or degree of homology may be adjusted upwards to correct for the conservative nature of the substitution. Means for making this adjustment are well known to those of skill in the art. See, e.g., Pearson, 1994, *Methods Mol. Biol.* 24:307-31 and 25:365-89 (herein incorporated by reference).

The following six groups each contain amino acids that are conservative substitutions for one another: 1) Serine (S), Threonine (T); 2) Aspartic Acid (D), Glutamic Acid (E); 3) Asparagine (N), Glutamine (Q); 4) Arginine (R), Lysine (K); 5) Isoleucine (I), Leucine (L), Methionine (M), Alanine (A), Valine (V), and 6) Phenylalanine (F), Tyrosine (Y), Tryptophan (W).

Sequence homology for polypeptides, which is also referred to as percent sequence identity, is typically measured using sequence analysis software. See, e.g., the Sequence Analysis Software Package of the Genetics Computer Group (GCG), University of Wisconsin Biotechnology Center, 910 University Avenue, Madison, Wis. 53705. Protein analysis software matches similar sequences using a measure of homology assigned to various substitutions, deletions and other modifications, including conservative amino acid substitutions. For instance, GCG contains programs such as "Gap" and "Bestfit" which can be used with default parameters to determine sequence homology or sequence identity between closely related polypeptides, such as homologous polypeptides from different species of organisms or between a wild-type protein and a mutein thereof. See, e.g., GCG Version 6.1.

A preferred algorithm when comparing a particular polypepitde sequence to a database containing a large number of sequences from different organisms is the computer program BLAST (Altschul et al., *J. Mol. Biol.* 215:403-410 (1990); Gish and States, *Nature Genet.* 3:266-272 (1993); Madden et al., *Meth. Enzymol.* 266:131-141 (1996); Altschul et al., *Nucleic Acids Res.* 25:3389-3402 (1997); Zhang and Madden, *Genome Res.* 7:649-656 (1997)), especially blastp or tblastn (Altschul et al., *Nucleic Acids Res.* 25:3389-3402 (1997)).

Preferred parameters for BLASTp are:

Expectation value: 10 (default); Filter: seg (default); Cost to open a gap: 11 (default); Cost to extend a gap: 1 (default); Max. alignments: 100 (default); Word size: 11 (default); No. of descriptions: 100 (default); Penalty Matrix: BLOWSUM62.

The length of polypeptide sequences compared for homology will generally be at least about 16 amino acid residues, usually at least about 20 residues, more usually at least about 24 residues, typically at least about 28 residues, and preferably more than about 35 residues. When searching a database containing sequences from a large number of different organisms, it is preferable to compare amino acid sequences. Database searching using amino acid sequences can be measured by algorithms other than blastp known in the art. For instance, polypeptide sequences can be compared using FASTA, a program in GCG Version 6.1. FASTA provides alignments and percent sequence identity of the regions of the best overlap between the query and search sequences. Pearson, *Methods Enzymol.* 183:63-98 (1990) (herein incorporated by reference). For example, percent sequence identity between amino acid sequences can be determined using FASTA with its default parameters (a word size of 2 and the PAM250 scoring matrix), as provided in GCG Version 6.1, herein incorporated by reference.

"Specific binding" refers to the ability of two molecules to bind to each other in preference to binding to other molecules in the environment. Typically, "specific binding" discriminates over adventitious binding in a reaction by at least two-fold, more typically by at least 10-fold, often at least 100-fold. Typically, the affinity or avidity of a specific binding reaction, as quantified by a dissociation constant, is about $10^{-7}$ M or stronger (e.g., about $10^{-8}$ M, $10^{-9}$ M or even stronger).

The term "region" as used herein refers to a physically contiguous portion of the primary structure of a biomolecule. In the case of proteins, a region is defined by a contiguous portion of the amino acid sequence of that protein.

The term "domain" as used herein refers to a structure of a biomolecule that contributes to a known or suspected function of the biomolecule. Domains may be co-extensive with regions or portions thereof; domains may also include distinct, non-contiguous regions of a biomolecule. Examples of protein domains include, but are not limited to, an Ig domain, an extracellular domain, a transmembrane domain, and a cytoplasmic domain. As used herein, the term "molecule" means any compound, including, but not limited to, a small molecule, peptide, protein, sugar, nucleotide, nucleic acid, lipid, etc., and such a compound can be natural or synthetic.

The term "high mannose" as used herein refers to a glycan structure on a glycoprotein which is natively produced by species of yeast and/or filamentous fungi, and generally has eight or more mannose residues.

As used herein, the term "molecule" means any compound, including, but not limited to, a small molecule, peptide, protein, sugar, nucleotide, nucleic acid, lipid, etc., and such a compound can be natural or synthetic.

The terms "α-mannosidase resistant glycans" and "recalcitrant α-mannose glycans" are used interchangeably herein and refer to glycan structure of a glycoprotein which are wholly or partially resistant to cleavage by alpha-mannosidases, such as with α-1,2; α-1,3; and/or α-1,6-mannosidases. Recalcitrant α-mannose glycans may include β-mannose, branched high mannose, α-1,4 mannose or uncharacterized mannose. These glycan structures therefore contribute to increased presence of high mannose glycan structures.

Unless otherwise defined, all technical and scientific terms used herein have the same meaning as commonly understood by one of ordinary skill in the art to which this invention pertains. Exemplary methods and materials are described below, although methods and materials similar or equivalent to those described herein can also be used in the practice of the present invention and will be apparent to those of skill in the art. All publications and other references mentioned herein are incorporated by reference in their entirety. In case of conflict, the present specification, including definitions, will control. The materials, methods, and examples are illustrative only and not intended to be limiting.

Throughout this specification and claims, the word "comprise" or variations such as "comprises" or "comprising", will be understood to imply the inclusion of a stated integer or group of integers but not the exclusion of any other integer or group of integers.

Identification of α-Mannosidase Resistant Gene

In an effort to express human-like glycoproteins in fungal systems, elimination of non-human glycosylation is desired. Fungal glycosylation is characterized by high mannose/non-human glycans. Determining the type of mannosylation is commonly the first step in eliminating undesired glycosylation events. The deletion of OCH1 in *P. pastoris* led to a decrease in hypermannosylation (Choi et al., 2003). Analysis by negative MALDI-TOF MS, revealed the presence of negative charges associated with these mannose groups. The subsequent deletion of the putative mannosylphosphate transferase genes, PNO1 and MNN4B, led to a strain devoid of mannosylphosphate (FIG. 2A) U.S. Pat. No. 7,259,007. Digestion of the remaining mannose groups by α-1,2 mannosidase and Jack Bean mannosidase further reduced the size of the mannans (FIG. 2B, FIG. 3) (Example 1). Despite these gene disruptions and digests with α-mannosidases, up to 20% of the N-glycans remained resistant. From sugar composition analysis, and the resistance of these mannose groups to α-1,2 mannosidase and Jack Bean mannosidase (α-1,2/ α-1,3/α-1, 6) it was deduced that these mannose structures are branched β-mannose, high mannose, α-1,4 mannose or uncharacterized mannose.

It was initially postulated that these resistant mannans result from mannosyltransferase activity, and it was thus speculated that the gene (or genes) responsible for these resistant mannans would have some homology to other mannosyltransferase genes. A C-terminal sequence from the *Saccharomyces cerevisiae* MNN4 gene was used to probe the *P. pastoris* genome (Example 2). By selecting genes encoding putative Type II membrane proteins (and thus, could be found on the Golgi membrane), a gene was identified that when disrupted, eliminates the resistant mannans after digest with α-1,2 mannosidase (FIG. 2D). We have named this gene AMR2 (alpha-mannosidase resistant). Accordingly, the present invention discloses a *P. pastoris* gene involved in mannosylation of glycoproteins as set forth in FIG. 1.

Nucleic Acid Sequences

In one aspect of the present invention, a gene involved in the mannosylation of N-glycans which are resistant to known α-mannosidases is identified and sequenced in *P. pastoris* (FIG. 1, Example 2). In one embodiment, a nucleic acid sequence encoding the *P. pastoris* AMR2 gene and variants thereof are provided. Disruption of the *P. pastoris* AMR2 gene is particularly useful for the reduction or elimination of α-mannosidase-resistant glycans on glycoproteins in a yeast strain. In another embodiment, the present invention provides a nucleic acid molecule comprising or consisting of a sequence which is a variant of the *P. pastoris* AMR2 gene having at least 72% identity to SEQ ID NO: 11. The nucleic acid sequence preferably has at least 75%, 80% or 85% identity to the wild type gene. Even more preferably, the nucleic acid sequence has 90%, 95%, 98%, 99%, 99.9% or even higher identity to the SEQ ID NO: 11.

According to other embodiments of the invention, the nucleic acid molecule of the invention encodes a polypeptide having the amino acid sequence shown in FIG. 1. Also provided is a nucleic acid molecule encoding a polypeptide sequence that is at least 72% identical to SEQ ID NO:12. Typically, the nucleic acid molecule of the invention encodes a polypeptide sequence of at least 75%, 80% or 85% identity to SEQ ID NO:12. Even more preferably, the encoded polypeptide has 90%, 95%, 98%, 99%, 99.9% or even higher identity to the SEQ ID NO:12.

In another aspect of the invention, the AMR2 gene involved in α-mannosidase-resistant mannosylation of N-glycans is homologous to three other genes in *P. pastoris*—AMR1, AMR3, AMR4 (FIG. 5), and has regions of homology to genes in the following species: eleven genes in *Candida albicans*, (eight shown in FIG. 5); eight genes in *Saccharomyces castellii* strain NRRL Y-12630; two genes in *Saccharomyces kluyveri* strain NRRL Y-12651, and three genes in *Aspergillus fumigatus* (Example 3). For the reduction or elimination of recalcitrant α-mannose glycans in other species, a person skilled in the art can identify AMR2 homologs from the genome of a given species, and disrupt the homologous gene or genes. One skilled in the art understands that it may be necessary to disrupt all homologous genes, or a combination of homologous genes found in any given species. More specifically, a skilled artisan recognizes that in order to reduce or eliminate α-mannosidase resistant N-glycans in other species, degenerate primers from the conserved sequences can be designed for PCR cloning of AMR2 homologs. Alternatively a probe could also be constructed for hybridization of the AMR2 homologs.

Host Cells

In another aspect of the invention, a host cell producing glycoproteins, which normally has α-mannosidase-resistant glycans, has been engineered to produce glycoproteins without α-mannosidase-resistant N-glycans. In one embodiment, a host cell producing therapeutic glycoproteins, which normally has mannosidase-resistant glycans, has been engineered to produce therapeutic glycoproteins without mannosidase-resistant glycans. In a preferred embodiment, the host cells of the invention have been mutated by recombination with a disruption, deletion or mutation of the isolated nucleic acid of the invention so that the α-mannosylation on glycans in the host cell is reduced compared to a host cell lacking the mutation. More preferably, α-mannosidase-resistance on N-glycans is eliminated. The host cell of the invention is preferably *Pichia pastoris* or *Pichia methanolica*, but other host cells, especially yeast cells, are also encompassed within the scope of the invention.

Figure 4:
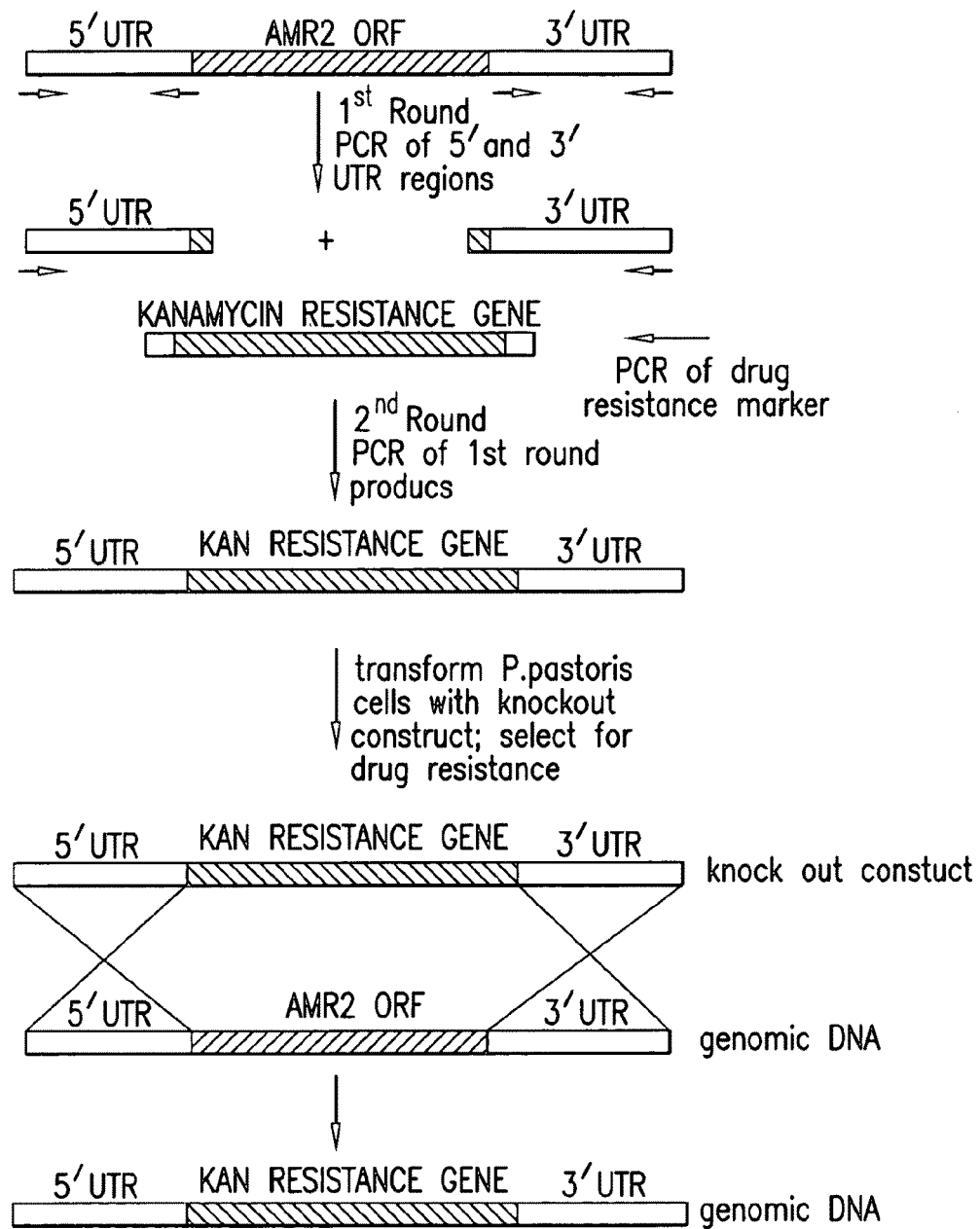
FIG. 4 illustrates the fusion PCR knock-out strategy of *P. pastoris* AMR2 using the drug resistance marker, kanamycin.

In some embodiments, the AMR2 gene in a yeast host cell is disrupted by the PCR knock-out strategy discussed in Example 3 and shown in FIG. 4. In other embodiments of the invention, host cells defective in α-mannosidase resistance activity are used to integrate one or more sequences or genes of interest into the host cell genome using nucleic acid molecules and/or methods of the invention. In a preferred embodiment, the sequences or genes of interest are integrated so as to disrupt an endogenous gene of the host cell. For example, the AMR2 gene is disrupted by a sequence of interest. Host cells containing the integration are easily identified by a selection marker, which in yeast are usually auxotrophic genes that allow growth of transformed cells on a medium lacking the specific amino acid or nucleotide or an antibiotic resistance gene, which allows for growth on media containing the corresponding antibiotic.

In another aspect of the invention, host cells transformed with the nucleic acid molecules or vectors of the invention, and descendants thereof, are provided. In some embodiments of the invention, these cells carry the nucleic acid sequences of the invention on vectors, which may but need not be freely replicating vectors. In other embodiments of the invention, the nucleic acids have been integrated into the genome of the host cells.

The disrupted AMR2 gene which encodes an activity involved in α-mannose resistance on glycans of glycoproteins is preferably from a yeast strain belonging to the genus *Pichia*. Yeasts belonging to the genus *Pichia* according to the present invention include for example, *Pichia pastoris, Pichia finlandica, Pichia trehalophila, Pichia koclamae, Pichia membranaefaciens, Pichia methanolica, Pichia minuta (Ogataea minuta, Pichia lindneri), Pichia opuntiae, Pichia thermotolerans, Pichi salictaria, Pichia guercum, Pichia pijperi, Pichia stiptis, Pichia* sp., and other yeasts, but not limited thereto. In yet another embodiment, genes carrying AMR2 activity and/or homology can be disrupted in one of the following hosts: *Saccharomyces castellii, Saccharomyces cerevisiae, Saccharomyces kluyveri, Saccharomyces* sp., *Hansenula polymorpha, Kluyveromyces* sp., *Kluyveromyces lactis, Candida albicans, Candida* sp., *Aspergillus fumigatus, Aspergillus nidulans, Aspergillus niger, Aspergillus oryzae, Trichoderma reesei, Chrysosporium lucknowense, Fusarium* sp., *Fusarium gramineum, Fusarium venenatum, Physcomitrella patens* and *Neurospora crassa*.

AMR2 Gene Encoding β-Mannosylation Activity

It was observed that some yeast species with homologs to this AMR2 gene also have β-mannosylation activity. Accordingly, in another aspect of the invention, the AMR2 gene encodes β-mannosyltransferase activity. In one embodiment, AMR2 encoding β-mannosyltransferase activity is disrupted individually and/or in combination with any of its homologs in *P. pastoris* or other fungal species, resulting in the reduction or elimination of α-mannosylation resistant glycans on glycoproteins.

The presence of β-mannosylation on O-glycans is discussed in the report by Trimble et al, 2003. Accordingly, in a further embodiment, α-mannosidase resistant O-glycans in *P. pastoris* and other species is reduced or eliminated with the disruption of the AMR2 gene and its homologs.

The following are examples which illustrate the compositions and methods of this invention. These examples should not be construed as limiting—the examples are included for the purposes of illustration only.

EXAMPLE 1

Jack Bean and α-1,2 Mannosidase Digestion of N-Glycans

The standard N-linked oligosaccharides (20 μg) was reconstituted in 100 μl HPLC grade water. A 10 μl aliquot was added to a 0.6 ml siliconized tube. The sample was evaporated to dryness. To the sample, 10 μl of 50 mM ammonium acetate was added, along with Jack Bean mannosidase (0.03 U) or α-1,2 mannosidase from *Trichoderma reseei* (0.03 mU, a gift from Dr Contreras R, Unit of Fundamental and Applied Molecular Biology, Department of Molecular Biology, Ghent University, Ghent, Belgium). The sample was incubated with the enzyme for 16 to 24 hr at 37° C. The sample was then evaporated to dryness. The sample was reconstituted in 10 μl of water. The sample was subsequently analyzed by MALDI-TOF MS.

Matrix Assisted Laser Desorption Ionization Time of Flight Mass Spectrometry

Molecular weights of the glycans were determined using a Voyager DE PRO linear MALDI-TOF (Applied Biosciences) mass spectrometer using delayed extraction. The dried glycans from each well were dissolved in 15 uL of water and 0.5 uL spotted on stainless steel sample plates and mixed with 0.5 uL of S-DHB matrix (9 mg/mL of dihydroxybenzoic acid, 1 mg/mL of 5-methoxysalicilic acid in 1:1 water/acetonitrile 0.1% TFA) and allowed to dry.

Ions were generated by irradiation with a pulsed nitrogen laser (337 nm) with a 4 ns pulse time. The instrument was operated in the delayed extraction mode with a 125 ns delay and an accelerating voltage of 20 kV. The grid voltage was 93.00%, guide wire voltage was 0.10%, the internal pressure was less than 5×10-7 torr, and the low mass gate was 875 Da. Spectra were generated from the sum of 100-200 laser pulses and acquired with a 2 GHz digitizer. $Man_5GlcNAc_2$ oligosaccharide was used as an external molecular weight standard. All spectra were generated with the instrument in the positive ion mode. The estimated mass accuracy of the spectra was 0.5%.

EXAMPLE 2

Identification and Sequence Analysis of AMR2 Gene from *Pichia pastoris*

The C-terminal part of *Saccharomyces cerevisiae* MNN4 gene (Genbank accession # P36044) containing a repetitive sequence rich in lysine and glutamic acid was used as a probe to blast against a *P. pastoris* genomic sequence (Integrated Genomics, Chicago, Ill.). Several DNA fragments with ORF's encoding proteins with similar lysine and glutamic acid rich repeats were identified. Among those one ORF was found to encode for a protein of 644 amino acids with putative N-terminal transmembrane domain and C-terminal tail rich in lysine and glutamic acid structurally resembling *S. cerevisiae* Mnn4p. Base on the phenotype analysis of the strain carrying mutated allele, the gene was named AMR2 (alpha-mannosidase resistant). Subsequent blast searches of *P. pastoris* genomic sequence revealed the presence of three more genes closely related to AMR2.

EXAMPLE 3

Deletion of AMR2 Gene in YAS137 Strain

Figure 3:
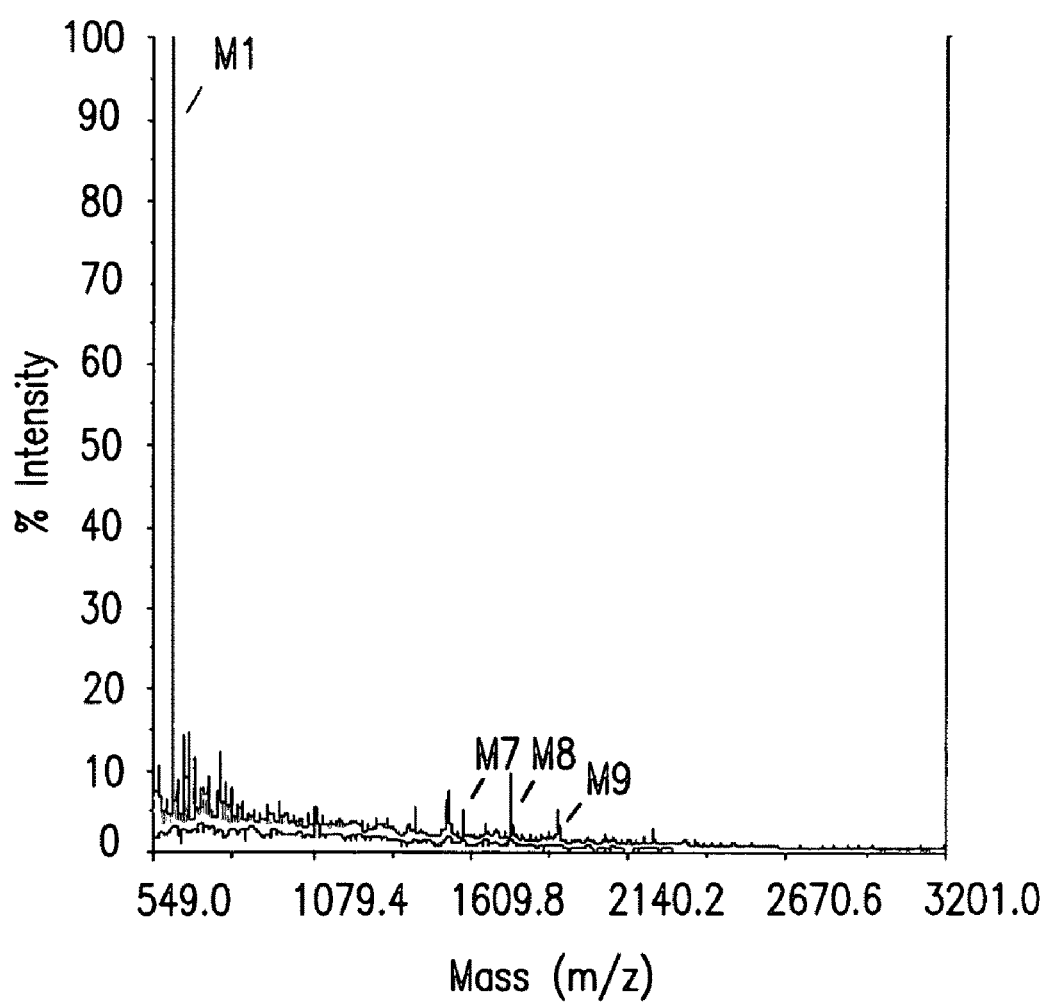
FIG. 3 MALDI-TOF MS spectra of the N-glycans of *P. pastoris* YAS137 after digestion with α-1,2 mannosidase and Jack Bean mannosidase.

*P. pastoris* strain YAS137 (Δoch1, Δpno1, Δmnn4b) (U.S. Pat. No. 7,259,007) was used as a host for the AMR2 gene knockout experiment. YAS137 produces charge free N-glycans without outer chain (FIG. 2A). When digested with α-1,2-mannosidase (FIG. 2B) and Jack Bean (with α-1,2/α-1,3/α-1,6 activity) mannosidases, a significant percentage of N-glycans purified from strain YAS137 can be converted to $Man_5GlcNAc_2$. However, up to 20% of the total N-glycans are recalcitrant to these α-mannosidases (FIG. 3). The amr2 deletion allele (amr2::Kan$^R$) was generated by the PCR overlap method (FIG. 4). Primers PBS1-2-C3 (SEQ ID NO: 1) (5'-TAATAGTGGAGAAA-CTTGCAAAGG-3') paired with PBS2-KO2 (SEQ ID NO: 2) (5'-GTGCTACCTAAAT-CGTATGTGTCGTTGAAGCTTCCCAATGATAGC-3'), and PBS1-2-KO3 (SEQ ID NO: 3) (5'-CTCCCTATAGT-GAGTCGTATTCATATGAT-GGGTGTTTGCTCACTC-3') paired with PBS1-2-KO4 (SEQ ID NO: 4) (5'-CTTGG-TTCAACGCAGCACTTTG-AC-3') were used to amplify the 5' and 3' flanking regions of the AMR2 gene from genomic DNA (genomic DNA was isolated from strain NRRL-Y11430). Primers PR29 (SEQ ID NO: 5) (5'-CACATAC-GATTTAG-GTGACAC-3') paired with PR32 (SEQ ID NO: 6) (5'-AATACGACTCACTATAGG-GAG-3') were used to amplify the Kan (G418) resistance marker from vector pUG6 (Goldstein and McCusker, 1999). Subsequently, primers PBS1-2-C3 and PBS1-2-KO4 were used in a second reaction with all three products from the first round of PCR reactions to generate an overlap product. The resulting fusion PCR product was used to transform strain YAS137. DNA for transformation was prepared by adding sodium acetate to a final concentration of 0.3 M. One hundred percent ice-cold ethanol was then added to a final concentration of 70% to the DNA sample. DNA was pelleted by centrifugation (12000 g×10 min) and washed twice with 70% ice-cold ethanol. The DNA was dried and then resuspended in 50 μl of 10 mM Tris, pH 8.0. YAS137 was prepared by expanding a yeast culture in BMGY (buffered minimal glycerol: 100 mM potassium phosphate, pH 6.0; 1.34% yeast nitrogen base; 4×10$^{-5}$% biotin; 1% glycerol) to an O.D. of ~2-6. The yeast were made electrocompetent by washing 3 times in 1M sorbitol and resuspending in ~1-2 mls 1M sorbitol. DNA (1-2 μg) was mixed with 50 μl of competent yeast and incubated on ice for 1 min. Yeast were then electroporated with a BTX Electrocell Manipulator 600 using the following parameters: 1.5 kV, 129 ohms, and 25 μF. One milliliter of YPDS (1% yeast extract, 2% peptone, 2% dextrose, 1M sorbitol) was added to the electroporated cells. Transformed yeast was subsequently plated on selective agar plates. Transformants were selected on YPD medium containing 200 μg/ml of G418 sulfate, GIBCO™. Proper integration of deletion allele amr2::Kan$^R$ was confirmed by PCR. Screening for knockouts was performed by PCR amplification of both the 5' and 3' portions of the knockout construct. PBS 1-C5 (SEQ ID NO: 7) (5'-TTTTCCTCA-AGCCTTCAAA-GACAG-3') and PTEF (SEQ ID NO: 8) (5'-AGCTGCGCA-CGTCAAGACTGT-CAA-GG-3') primers were used to screen the 5' portion of the knockout construct while PBS 1-2-C2 (SEQ ID NO: 9) (5'-TACCGATACATAC-GTAGCCAACAC-3') and KAN10 (SEQ ID NO: 10) (5'-TCGCTATACTGCTG-TCGATTC-GATAC-3') primers were used to screen the 3' portion of the knockout construct. Observation of a PCR product in both screens is indicative of a successful knockout of the AMR2 gene since primers PTEF and KAN10 anneal at the 5' and 3' ends of the drug resistance marker sequence, respectively; and PBS 1-C5 and PBS1-2-C2 are complimentary to sequences in the genome that flank the 5' and 3' regions of DNA used in the knockout construct. The new (Δoch1, Δpno1, Δmnn4b, Δamr2) strain was designated PBP130.

PCR Amplification

An Eppendorf Mastercycler was used for all PCR reactions. PCR reactions contained template DNA, 125 μM dNTPs, 0.2 μM each of forward and reverse primer, Ex Taq polymerase buffer (Takara Bio Inc.), and Ex Taq polymerase (Takara Bio Inc.). The DNA fragments 5' to the predicted AMR2 gene, 3' to the predicted AMR2 gene, and the drug resistance marker were amplified with 30 cycles of 10 sec at 98° C., 10 sec at 52° C. and 2 min at 72° C. with an initial denaturation step of 2 min at 94° C. and a final extension step of 10 min at 72° C. PCR samples were separated by agarose gel electrophoresis and the DNA bands were extracted and purified using a Gel Extraction Kit from Qiagen. All DNA purifications were eluted in 10 mM Tris, pH 8.0.

Searches and Alignments

A BLAST search to obtain sequences from completed and incomplete fungal genomes at NCBI, was carried out, leading to the identification of AMR2 homologs as discussed in the Details of the Invention. The alignment shown in FIG. 5 was constructed using the Megalign program (DNAStar) and ClustalW algorithm.

EXAMPLE 4

Determination of α-Mannosidase Resistant N-Glycans in *P. pastoris*

N-linked glycans in YAS137 and PBP130 were analyzed by secreting a His-tagged reporter protein expressed under the control of the methanol inducible AOX1 promoter. The reporter protein, K3, contains a single N-linked glycosylation site. Briefly, a shake flask containing BMGY was inoculated with a fresh culture of YAS-130 and grown to an O.D. of ~20. The culture was centrifuged and the cell pellet washed with BMMY (buffered minimal methanol: same as BMGY except 0.5% methanol instead of 1% glycerol). The cell pellet was resuspended in BMMY to a volume ⅕ of the original BMGY culture and placed in a shaker for 24 h. The secreted protein was harvested by pelleting the biomass by centrifugation and transferring the culture medium to a fresh tube. The His-tagged K3 protein was then purified on a Ni-affinity column and digested with PNGase (Choi et al., 2003).

EXAMPLE 5

Analysis of Man10 and Man11/12

Structural analysis of the glycans recalcitrant to α-mannosidase digestion disclosed at least one β1,2-mannosyl residue linked to a core mannose oligosaccharide. Structure I shows a proposed β-mannosyl residue 13 shown on branch 5, which can be definitively linked to that chain, and is likely to be an integral part of the high-mannose structure. The residues on the following glycan structure (Structure I) was numbered based on the paper by Ziegler et al, (Ziegler, F. D., J. Cavanagh, C. Lubowski, R. B. Trimble, 1999, Glycobiology 9:497-505), with additional numbers (13,14,15) added arbitrarily.

Data from three samples were analyzed for the presence of β-mannosyl residues.

Sample 1: "man10"—this was the original sample described as a man9/10 mixture

Sample 2: "man11"—this was a second preparation described as man11/man12 mixture from P4 fractions 63-66 with estimated 50% man11, 15% man 12.

Sample3: "man10_digest"—this was a third preparation wherein the original man11/man12 mixture was treated with a1,2-mannosidase to trim back to man9 or man10.

A fourth sample containing the core man8/man9 mixture was also examined.

Samples were lyophilized from D2O, and redissolved into 200 uL or 500 uL D2O.

NMR data were collected on Varian Inova 600 MHz and 800 MHz spectrometers at 25C. Standard experiments from the Varian library (gradient COSY, TOCSY, NOESY, gradient HSQC and HMBC) were used for characterization.

Evidence for β-Mannosyl Residues:

All three samples have NMR signals that are consistent with β-anomers. Three spectral features support this argument: chemical shifts, H1-H2 scalar coupling, and intra-molecular NOE measurements.

Proton Chemical Shifts.

The chemical shift values of the anomeric protons for α-mannosyl residues are typically greater than 5.0 ppm, whereas the β-mannosyl residues are usually less than 5.0 ppm. There are exceptions, such as a-mannosyl residues 3, 4 and 12, so this alone does not prove anomeric configuration.

Analysis showing the anomeric region of proton 1D spectra of the four samples, revealed two peaks 13 and 13t, which correspond to a β-mannosyl residue linked 1-2 to 11, where 13t is a terminal residue, and 13 seems further substituted with an α-mannosyl residue 14. One can compare these spectra to NMR data from high-mannose structures found in Ziegler et al., which show only the core residues 3 and 4, and the residue 12, in the chemical shift region below 5 ppm.

Additional chemical shifts were extracted from the 2D TOCSY data, which shows distinct H1,H2,H3,H4 and H5 signals from residue 13 which correspond closely to data reported in Trinel et al, JBC 1999 and Nitz et al, JBC 2002. The signals from the terminal residue 13t are not as well separated but have similar shifts (see Table 1).

The 2D TOCSY (a proton-proton correlated map) showed crosspeaks belonging to the β-Man 13 residue (data not shown). Chemical shifts of β-mannosyl residues and the literature values are listed in Table 1.

Structure I

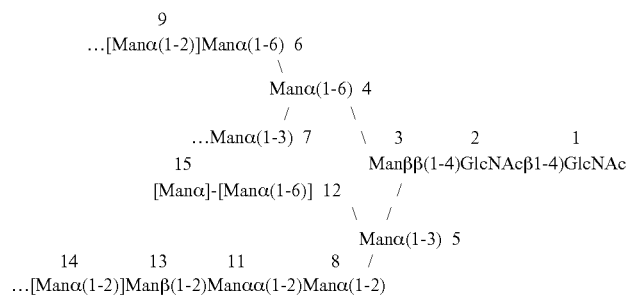

TABLE 1

|  | H1 | H2 | H3 | H4 | H5 |
|---|---|---|---|---|---|
| β-man 13 | 4.90 | 4.35 | 3.75 | 3.64 | 3.40 |
| β-man 13t | 4.86 | 4.27 | 3.67 | 3.47 | 3.40 |
| Trinel et al. | 4.90-5.05 | 4.16-4.41 | 3.63-3.73 | 3.47-3.59 | 3.41 |
| Nitz et al. | 4.95 | 4.42 | 3.62 | 3.56 | |

Chemical shifts for a-Mannosyl residues have generally the same order, but the values for H2 are typically ~0.1 ppm lower, H3 are ~0.1 ppm higher and H5 are ~0.2 ppm higher. (Trinel, P.-A., Y. Plancke, P. Gerold, T. Jouault, F. Delplace, R. T. Schwarz, G. Strecker, and D. Poulain, 1999, *J. Biol. Chem.* 274:30520-30526) (Nitze. M, C.-C. Ling, A. Otter, J. E. Cutler, D. R. Bundle, 2002, *J. Biol. Chem.*, 277:3440-3446)

NOE Crosspeaks.

The β-anomeric proton is on the same face of the pyranose ring as the H3 and H5 and about 2.4 Angstroms apart, whereas the α-anomeric proton is on the opposite face, and closer to 4 Ang. from either H3 or H5. Therefore, one expects a strong NOE signal between H1 and H3 and H5 in the β-anomer. This is clearly shown in the NOESY data (not shown), where the spectrum shows the NOE crosspeaks that arise from through space interactions and are highly distance dependent. The horizontal line at 4.895 ppm corresponds to the H1 of the β-man 13 residue (data not shown). The vertical lines confirm the assignment of these peaks to specific resonances, as determined by the TOCSY experiment in the top panel. The strong peaks H3 and H5 are due to intra-residue NOEs between H1 and H3 or H5, confirming the β-anomeric assignment (data not shown).

H1 to H2 Scalar Coupling ('Splitting' of Peaks)

The magnitude of the proton scalar coupling that gives rise to 'splittings' of resonances and multiplet structure is related to the relative orientation of the protons involved. It can thus be an indication of anomeric configuration.

The H1-H2 scalar coupling in α-mannosyl residues is about 1.5 Hz, whereas the β-anomer is <1 Hz. In spectra with very narrow lines you can see the splitting for the α-anomer, whereas the β-anomer is too small and the signals look like singlets. In these data, the linewidth was not optimal, so both sets of peaks look like singlets. However, the pattern and intensity of peaks in the 2D TOCSY (data not shown) is also dependent on the magnitude of the coupling. A region from the TOCSY spectrum shows where the horizontal lines correspond to H1 signals, and the crosspeaks are from other protons in the respective residues. First the peaks in the H2 region that are linked to β-Man residues (3,13,13t) are lower intensity than the α-Man peaks (e.g. 4). The intensity is a rough indication of the efficiency of the signal transfer and therefore the size of the coupling constant.

The α-anomers also show additional crosspeaks from H1 to H3 and sometimes H4—this means that the scalar coupling between H1 and H2 is sufficiently large to allow transfer of the signal beyond H2. The β-anomers, on the other hand, show only H1 to H2 crosspeaks; since the coupling is so small the transfer of signal is very inefficient and doesn't continue to other protons in the ring. The patterns for 13, 13t and 3 are the same, but clearly different from the other mannosyl residues.

Evidence for Linkage Position of β-Mannosyl 13(t).

Changes in H1 and H2 Chemical Shifts.

For a known high-mannose structure, it is usually sufficient to compare the H1 and H2 proton chemical shifts with standard literature values to arrive at a structure. In this case, anomalous signals required more effort to establish linkages. However, there were some peaks that could be assigned to the core structure, such as shown for the Man8/9 spectrum. Comparing the Man8/9 and the Man9/10 spectra (data not shown), there are many differences, including the new signals 13 and 13t, which have been described above as β-mannosyl residues.

Comparing the spectra of samples Man9/10 and Man11/12, the terminal α-mannosyl residues similar to 9 have returned. This would suggest the peak labeled 6,12 in the Man9/10 spectrum is likely to be terminal 6, since it is expected to shift upon substitution with another α-mannose. It returns to the original position in the mannosidase digested sample, Man10-digest. The carbon-proton correlated data (HSQC, HMBC spectra not shown) from the Man11, and Man 10-digest samples confirms that this residue is connected in a 1-6 linkage.

The signal labeled 14, is proposed to be an α-mannosyl residue linked to 13, rather than a substituted mannosyl residue 7, as is seen in typical Man9 structures. This is based on the NOE data discussed below. However, to account for the chemical shift of the anomeric proton, it is probably further substituted.

Analysis of NOE Data.

The primary data for determining linkage sites are from NOE spectra, which indicates protons that are close in space. Therefore, in addition to intra-residue NOE crosspeaks, one can also observe inter-residue crosspeaks, which usually indicate the linkage position. In the case of Man(1-2) linkages, one observes crosspeaks between H1 and H2 in the same residue, between H1 and H2 of the glycosidically linked residue, and often between H1 and H1 of the glycosidically linked residue.

Regions from the NOESY and TOCSY spectrum of the man10 sample were analyzed (data not shown). In the top panel, the peaks represent the correlation between H1 and H2 of the identified mannosyl residues. In the middle panel, the signal labeled 11 shows an NOE correlation (box) between H1 and H2 of mannosyl residue 8, consistent with its assignment. If we examine the NOE crosspeaks from the anomeric protons of residues 13 and 13t, there are correlations with H2 of mannosyl residue 11. This links the β-mannosyl residues to the 1-3 branch of the core oligosaccharide. The lower panel shows an additional strong NOE correlation between H1 of 13t and H1 of 11, also consistent with a β(1-2) linkage.

Additional support for this structural fragment comes from the unusual chemical shift of the H2 of mannosyl residue 11; its value is consistent with data from Trimble et al (Trimble, R. B., C. Lubowski, C. Hauer III, R. Stack, L. McNaughton, T. Gemmill, and S. Anand Kumar, 2004, Glycobiology 14:265-274)) showing chemical shifts of 4.26 ppm for α-mannosyl residues 2—substituted by β-man. In addition, proton-carbon correlated data (HSQC and HMBC spectra, not shown) indicate that the carbon chemical shifts of the C2 of mannosyl 11 (as well as 8 and 5, for example) are at high values (~82-84 ppm) characteristic of carbons in glycosidic linkages.

We conclude that at least one β-mannosyl residue can be shown to be linked 1-2 to a core mannose oligosaccharide. There may be multiple linkage sites for the β-mannosyl residues, and they themselves may be substituted.

REFERENCES

Choi, B-K. et al. 2003. Use of combinatorial genetic libraries to humanize N-linked glycosylation in yeast *Pichia pastoris*. *Proc. Natl. Acad. Sci.* 100; 5022-5027.

Cregg, J. M. et al. 2000. Recombinant protein expression in *Pichia pastoris*. *Mol. Biotechnol.* 16; 23-52.

Cutler, J. E. 2001 N-glycosylation of yeast, with emphasis on *Candida albicans*. *Med. Mycology.* 39; S75-S86.

Han, Y., Kanbe, T., Cherniak, R. and Cutler, J. E. 1997. Biochemical characterization of *Candida albicans* epitopes that can elicit protective and nonprotective antibodies. *Infect. Immun.* 65; 4100-4107.

Joualt, T., Delaunoy, C. Sendid, B., Ajana, R. and Poulain, D. 1997. Differential humoral response against α- and β-linked mannose residues associated with tissue invasion by *Candida albicans*. *Clin. Diagn. Lab. Immunol.* 4; 328-333.

Kobayashi, H., Shibata, N. and Suzuki, S. 1986. Acetolysis of *Pichia pastoris* IFO 0948 Strain Mannan Containing α-1,2 and β-1,2 Linkages Using Acetolysis medium of Low Sulfuric Acid Concentration. *Arch. Biochem. Biophys.* 245; 494-508.

Kobayashi, H et al. 1989. Structural study of phosphomannan of yeast-form cells of *Candida albicans* J-1012 strain with special reference to application of mild acetolysis. *Arch. Biochem. Biophys.* 272; 364-375.

Kobayashi, H. et al. 1992. Structural study of a cell wall mannan-protein complex of the pathogenic yeast *Candida glabrata* IFO 0622 strain. *Arch. Biochem. Biophys.* 294; 662-669.

Kobayashi, H. et al. 1994. Structural modification of cell wall mannans of *Candida albicans* serotype A strains grown in yeast extract-Sabouraud liquid medium under acidic conditions. *Infect. Immun.* 62; 968-973.

Rosenfeld, L. and Ballou, C. 1974. Genetic Control of Yeast Mannan Structure. *J. Biol. Chem.* 249; 2319-2321.

Shibata, N., Ichikawa, T., Tojo, M. et al. 1985. Immunochemical study on the mannans of *Candida albicans* NIH A-207, NIH B-792 and J-1012 strains prepared by fractional precipitation with cetyltrimethylammonium bromide. *Arch. Biochem. Biophys.* 243; 338-348.

Shibata, N., Hisamichi, K., Kobayashi, H., and Suzuki, S. 1993a. Complete assignment of 1H and 13C nuclear magnetic resonance chemical shifts of beta-1,2-linked mannooligosaccharides isolated from the phosphomannan of the pathogenic yeast *Candida albicans* NIH B-792 strain. *Arch Biochem Biophys.* 302; 113-117.

Shibata, N., Hisamichi, K., Kobayashi, H., and Suzuki, S. 1993b. Structural study of a cell-wall mannan of *Saccharomyces kluyveri* IFO 1685 strain. Presence of a branched side chain and beta-1,2-linkage. *Eur J. Biochem.* 217; 1-12.

Suzuki, A. et al. 1997. Charcterization of b-1,2 Mannosyltransferase in *Candida guilliermondii* and Its Utilization in the Synthesis of Novel Oligosaccharides. *J. Biol. Chem.* 272; 16822-16828.

Takeuchi, Makato. 1997. Trial for Molecular Breeding of Yeast for the Production of Glycoprotein Therapeutics. *Trends in Glycoscience and Glycotechnology.* 9; S29-S35.

Trimble, R. B. et al. 2004. Characterization of N— and O— linked glycosylation of recombinant human bile salt-stimulated lipase secreted by *Pichia pastoris*. *Glycobiology.* 14; 265-274.

What is claimed is:

1. A modified *Pichia pastoris* host cell characterized in that the host cell has been modified to reduce expression of a functional gene product of a nucleic acid sequence encoding a polypeptide having the amino acid sequence set forth in SEQ ID NO:12.

2. The modified host cell of claim 1 wherein said modified host cell comprises a disruption or deletion in the nucleic acid sequence encoding a polypeptide having the amino acid sequence set forth in SEQ ID NO:12.

3. The host cell of claim 1, wherein the host cell further comprises deletion of a functional gene product encoding an alpha-1,6-mannosyltransferase activity.

4. The host cell of claim 1, wherein the host cell further comprises deletion of a functional gene product encoding mannosylphosphate transferase activity.

5. A modified *Pichia pastoris* host cell characterized in that the host cell has been modified to reduce expression of a β-mannosyltransferase activity.

6. The modified host cell of claim 5 wherein said modified host cell comprises a disruption or deletion in the nucleic acid sequence encoding the β-mannosyltransferase activity.

7. The host cell of claim 5, wherein the host cell further comprises deletion of a functional gene product encoding an alpha-1,6-mannosyltransferase activity.

8. The host cell of claim 5, wherein the host cell further comprises deletion of a functional gene product encoding mannosylphosphate transferase activity.

* * * * *

```
                      SEQUENCE LISTING

<160> NUMBER OF SEQ ID NOS: 15

<210> SEQ ID NO 1
<211> LENGTH: 24
<212> TYPE: DNA
<213> ORGANISM: Artificial
<220> FEATURE:
<223> OTHER INFORMATION: degenerate oligonucleotide primer

<400> SEQUENCE: 1
taatagtgga gaaacttgca aagg                                            24

<210> SEQ ID NO 2
<211> LENGTH: 45
<212> TYPE: DNA
<213> ORGANISM: Artificial
<220> FEATURE:
<223> OTHER INFORMATION: degenerate oligonucleotide primer

<400> SEQUENCE: 2
gtgctaccta aatcgtatgt gtcgttgaag cttcccaatg atagc                     45

<210> SEQ ID NO 3
<211> LENGTH: 45
<212> TYPE: DNA
<213> ORGANISM: Artificial
<220> FEATURE:
<223> OTHER INFORMATION: degenerate oligonucleotide primer

<400> SEQUENCE: 3
```

```
ctccctatag tgagtcgtat tcatatgatg ggtgtttgct cactc            45
```

```
<210> SEQ ID NO 4
<211> LENGTH: 24
<212> TYPE: DNA
<213> ORGANISM: Artificial
<220> FEATURE:
<223> OTHER INFORMATION: degenerate oligonucleotide primer

<400> SEQUENCE: 4
cttggttcaa cgcagcactt tgac                                  24
```

```
<210> SEQ ID NO 5
<211> LENGTH: 21
<212> TYPE: DNA
<213> ORGANISM: Artificial
<220> FEATURE:
<223> OTHER INFORMATION: degenerate oligonucleotide primer

<400> SEQUENCE: 5
cacatacgat ttaggtgaca c                                     21
```

```
<210> SEQ ID NO 6
<211> LENGTH: 21
<212> TYPE: DNA
<213> ORGANISM: Artificial
<220> FEATURE:
<223> OTHER INFORMATION: degenerate oligonucleotide primer

<400> SEQUENCE: 6
aatacgactc actataggga g                                     21
```

```
<210> SEQ ID NO 7
<211> LENGTH: 24
<212> TYPE: DNA
<213> ORGANISM: Artificial
<220> FEATURE:
<223> OTHER INFORMATION: degenerate oligonucleotide primer

<400> SEQUENCE: 7
ttttcctcaa gccttcaaag acag                                  24
```

```
<210> SEQ ID NO 8
<211> LENGTH: 26
<212> TYPE: DNA
<213> ORGANISM: Artificial
<220> FEATURE:
<223> OTHER INFORMATION: degenerate oligonucleotide primer

<400> SEQUENCE: 8
agctgcgcac gtcaagactg tcaagg                                26
```

```
<210> SEQ ID NO 9
<211> LENGTH: 24
<212> TYPE: DNA
<213> ORGANISM: Artificial
<220> FEATURE:
<223> OTHER INFORMATION: degenerate oligonucleotide primer

<400> SEQUENCE: 9
taccgataca tacgtagcca acac                                  24
```

```
<210> SEQ ID NO 10
<211> LENGTH: 26
<212> TYPE: DNA
<213> ORGANISM: Artificial
```

<220> FEATURE:
<223> OTHER INFORMATION: degenerate oligonucleotide primer

<400> SEQUENCE: 10
tcgctatact gctgtcgatt cgatac                                          26

<210> SEQ ID NO 11
<211> LENGTH: 1935
<212> TYPE: DNA
<213> ORGANISM: Pichia pastoris

<400> SEQUENCE: 11

| | | | | | |
|---|---|---|---|---|---|
| atgagaacac | gactcaactt | cctgctgctc | tgtattgcca | gtgttttgtc | tgtgatttgg | 60 |
| atcggagtcc | tccttacttg | gaatgataat | aatcttggcg | gaatctccct | aaacggaggc | 120 |
| aaggattctg | cctatgatga | tctgctatca | ttgggaagct | tcaacgacat | ggaggtcgac | 180 |
| tcctatgtca | ccaacatcta | cgacaatgct | ccagtgctag | gatgtacgga | tttgtcttat | 240 |
| catggattgt | tgaaagtcac | cccaaagcat | gacttagctt | gcgatttgga | gttcataaga | 300 |
| gctcagattt | tggacattga | cgtttactcc | gccataaaag | acttagaaga | taaagccttg | 360 |
| actgtaaaac | aaaaggttga | aaaacactgg | tttacgtttt | atggtagttc | agtctttctg | 420 |
| cccgaacacg | atgtgcatta | cctggttaga | cgagtcatct | tttcggctga | aggaaaggcg | 480 |
| aactctccag | taacatctat | catagttgct | cagatatatg | acaaaaactg | aacgagtta | 540 |
| aatggccatt | tcttggacat | cctgaaccca | aatactggga | aggtccagca | caacacgttt | 600 |
| ccacaagttc | ttcctattgc | aaccaatttt | gtcaaaggta | agaagtttcg | tggggcagaa | 660 |
| gatcctagag | ttgttttgag | aaagggccgt | tttggacctg | atccttggt | gatgttcaac | 720 |
| tccctaactc | aagataacaa | acgtaggaga | atttttacca | tttctccatt | tgaccagttc | 780 |
| aaaacagtca | tgtacgacat | taaagactat | gagatgccca | ggtatgaaaa | gaactgggtc | 840 |
| ccattttct | taaagacaa | tcaggaggca | gttcattttg | tttactcttt | caaccctctg | 900 |
| agagtactca | aatgcagtct | tgatgacggc | tcatgtgata | ttgtgtttga | gataccgaaa | 960 |
| gttgactcca | tgtcgtctga | gttgcgtggt | gccacaccta | tgatcaatct | tcctcaggca | 1020 |
| attccgatgg | cgaaggacaa | agagatctgg | gtttcattcc | ccagaacgag | aattgcaaat | 1080 |
| tgtggttgct | ccaggacgac | atacagacca | atgctgatgc | tctttgtcag | agaaggttca | 1140 |
| aatttctttg | ttgaactctt | gtccacctct | cttgattttg | gtctggaggt | tttaccgtat | 1200 |
| tcaggaaacg | gattaccatg | cagtgcggac | cattccgttt | taatcccaaa | tagcattgat | 1260 |
| aactgggaag | tcgtagatag | caatggagac | gatatcttga | cattgtcatt | cagtgaggcg | 1320 |
| gacaagagta | cctctgtgat | tcatatcaga | gggctgtata | actatctatc | tgaactggat | 1380 |
| ggctatcaag | tccagaagc | agaggatgaa | cataatttcc | agcgtatcct | gagtgactta | 1440 |
| cattttgaca | caaaaccac | ggtaaacaat | tttataaaag | tacaatcatg | tgcactagat | 1500 |
| gctgccaaag | gttattgtaa | agaatatggg | cttactcgtg | gggaggcaga | acgaagaagg | 1560 |
| agggtcgctg | aggagagaaa | gaagaaggag | aaagaggaag | aagaaaaaaa | gaaaagaaa | 1620 |
| gaaaagaag | aagaagagaa | aaagaggatt | gaagaggaga | agaagaagat | tgaagaaaag | 1680 |
| gaacgaaagg | agaaagagaa | agaagaagcg | gagagaaaaa | agctgcaaga | aatgaaaaag | 1740 |
| aaacttgagg | aaatcacaga | aaaacttgaa | aaaggccaga | ggaataaaga | gatagatcca | 1800 |
| aaagagaagc | aaagggaaga | agaagaaaga | aaggagagag | tcaggaaaat | agcggagaaa | 1860 |
| caaaggaagg | aggcggaaaa | gaaggaggct | gaaaaaaagg | caaatgacaa | aaaggatcta | 1920 | aaaataagac agtag                                                                          1935

<210> SEQ ID NO 12
<211> LENGTH: 644
<212> TYPE: PRT
<213> ORGANISM: Pichia pastoris

<400> SEQUENCE: 12

```
Met Arg Thr Arg Leu Asn Phe Leu Leu Cys Ile Ala Ser Val Leu
1               5                   10                  15

Ser Val Ile Trp Ile Gly Val Leu Leu Thr Trp Asn Asp Asn Leu
            20                  25                  30

Gly Gly Ile Ser Leu Asn Gly Gly Lys Asp Ser Ala Tyr Asp Asp Leu
        35                  40                  45

Leu Ser Leu Gly Ser Phe Asn Asp Met Glu Val Asp Ser Tyr Val Thr
50                  55                  60

Asn Ile Tyr Asp Asn Ala Pro Val Leu Gly Cys Thr Asp Leu Ser Tyr
65                  70                  75                  80

His Gly Leu Leu Lys Val Thr Pro Lys His Asp Leu Ala Cys Asp Leu
                85                  90                  95

Glu Phe Ile Arg Ala Gln Ile Leu Asp Ile Asp Val Tyr Ser Ala Ile
            100                 105                 110

Lys Asp Leu Glu Asp Lys Ala Leu Thr Val Lys Gln Lys Val Glu Lys
        115                 120                 125

His Trp Phe Thr Phe Tyr Gly Ser Ser Val Phe Leu Pro Glu His Asp
    130                 135                 140

Val His Tyr Leu Val Arg Arg Val Ile Phe Ser Ala Glu Gly Lys Ala
145                 150                 155                 160

Asn Ser Pro Val Thr Ser Ile Ile Val Ala Gln Ile Tyr Asp Lys Asn
                165                 170                 175

Trp Asn Glu Leu Asn Gly His Phe Leu Asp Ile Leu Asn Pro Asn Thr
            180                 185                 190

Gly Lys Val Gln His Asn Thr Phe Pro Gln Val Leu Pro Ile Ala Thr
        195                 200                 205

Asn Phe Val Lys Gly Lys Lys Phe Arg Gly Ala Glu Asp Pro Arg Val
    210                 215                 220

Val Leu Arg Lys Gly Arg Phe Gly Pro Asp Pro Leu Val Met Phe Asn
225                 230                 235                 240

Ser Leu Thr Gln Asp Asn Lys Arg Arg Ile Phe Thr Ile Ser Pro
                245                 250                 255

Phe Asp Gln Phe Lys Thr Val Met Tyr Asp Ile Lys Asp Tyr Glu Met
            260                 265                 270

Pro Arg Tyr Glu Lys Asn Trp Val Pro Phe Leu Lys Asp Asn Gln
        275                 280                 285

Glu Ala Val His Phe Val Tyr Ser Phe Asn Pro Leu Arg Val Leu Lys
    290                 295                 300

Cys Ser Leu Asp Asp Gly Ser Cys Asp Ile Val Phe Glu Ile Pro Lys
305                 310                 315                 320

Val Asp Ser Met Ser Ser Glu Leu Arg Gly Ala Thr Pro Met Ile Asn
                325                 330                 335

Leu Pro Gln Ala Ile Pro Met Ala Lys Asp Lys Glu Ile Trp Val Ser
            340                 345                 350

Phe Pro Arg Thr Arg Ile Ala Asn Cys Gly Cys Ser Arg Thr Thr Tyr
        355                 360                 365
```

-continued

```
Arg Pro Met Leu Met Leu Phe Val Arg Glu Gly Ser Asn Phe Phe Val
    370                 375                 380

Glu Leu Leu Ser Thr Ser Leu Asp Phe Gly Leu Glu Val Leu Pro Tyr
385                 390                 395                 400

Ser Gly Asn Gly Leu Pro Cys Ser Ala Asp His Ser Val Leu Ile Pro
                405                 410                 415

Asn Ser Ile Asp Asn Trp Glu Val Val Asp Ser Asn Gly Asp Asp Ile
            420                 425                 430

Leu Thr Leu Ser Phe Ser Glu Ala Asp Lys Ser Thr Ser Val Ile His
        435                 440                 445

Ile Arg Gly Leu Tyr Asn Tyr Leu Ser Glu Leu Asp Gly Tyr Gln Gly
    450                 455                 460

Pro Glu Ala Glu Asp Glu His Asn Phe Gln Arg Ile Leu Ser Asp Leu
465                 470                 475                 480

His Phe Asp Asn Lys Thr Thr Val Asn Asn Phe Ile Lys Val Gln Ser
                485                 490                 495

Cys Ala Leu Asp Ala Ala Lys Gly Tyr Cys Lys Glu Tyr Gly Leu Thr
            500                 505                 510

Arg Gly Glu Ala Glu Arg Arg Arg Val Ala Glu Gly Arg Lys Lys
        515                 520                 525

Lys Glu Lys Glu Glu Glu Lys Lys Lys Lys Glu Lys Glu Glu
530                 535                 540

Glu Glu Lys Lys Arg Ile Glu Glu Lys Lys Ile Glu Glu Lys
545                 550                 555                 560

Glu Arg Lys Glu Lys Glu Lys Glu Ala Glu Arg Lys Lys Leu Gln
                565                 570                 575

Glu Met Lys Lys Lys Leu Glu Glu Ile Thr Glu Lys Leu Glu Lys Gly
            580                 585                 590

Gln Arg Asn Lys Glu Ile Asp Pro Lys Glu Lys Gln Arg Glu Glu Glu
        595                 600                 605

Glu Arg Lys Glu Arg Val Arg Lys Ile Ala Glu Lys Gln Arg Lys Glu
    610                 615                 620

Ala Glu Lys Lys Glu Ala Glu Lys Lys Ala Asn Asp Lys Lys Asp Leu
625                 630                 635                 640

Lys Ile Arg Gln
```

<210> SEQ ID NO 13
<211> LENGTH: 652
<212> TYPE: PRT
<213> ORGANISM: Pichia pastoris

<400> SEQUENCE: 13

```
Met Val Asp Leu Phe Gln Trp Leu Lys Phe Tyr Ser Met Arg Arg Leu
1               5                   10                  15

Gly Gln Val Ala Ile Thr Leu Val Leu Leu Asn Leu Phe Val Phe Leu
            20                  25                  30

Gly Tyr Lys Phe Thr Pro Ser Thr Val Ile Gly Ser Pro Ser Trp Glu
        35                  40                  45

Pro Ala Val Val Pro Thr Val Phe Asn Glu Ser Tyr Leu Asp Ser Leu
50                  55                  60

Gln Phe Thr Asp Ile Asn Val Asp Ser Phe Leu Ser Asp Thr Asn Gly
65                  70                  75                  80

Arg Ile Ser Val Thr Cys Asp Ser Leu Ala Tyr Lys Gly Leu Val Lys
                85                  90                  95
```

-continued

```
Thr Ser Lys Lys Lys Glu Leu Asp Cys Asp Met Ala Tyr Ile Arg Arg
            100                 105                 110

Lys Ile Phe Ser Ser Glu Glu Tyr Gly Val Leu Ala Asp Leu Glu Ala
            115                 120                 125

Gln Asp Ile Thr Glu Glu Gln Arg Ile Lys Lys His Trp Phe Thr Phe
            130                 135                 140

Tyr Gly Ser Ser Val Tyr Leu Pro Glu His Glu Val His Tyr Leu Val
145                 150                 155                 160

Arg Arg Val Leu Phe Ser Lys Val Gly Arg Ala Asp Thr Pro Val Ile
                165                 170                 175

Ser Leu Leu Val Ala Gln Leu Tyr Asp Lys Asp Trp Asn Glu Leu Thr
                180                 185                 190

Pro His Thr Leu Glu Ile Val Asn Pro Ala Thr Gly Asn Val Thr Pro
                195                 200                 205

Gln Thr Phe Pro Gln Leu Ile His Val Pro Ile Glu Trp Ser Val Asp
            210                 215                 220

Asp Lys Trp Lys Gly Thr Glu Asp Pro Arg Val Phe Leu Lys Pro Ser
225                 230                 235                 240

Lys Thr Gly Val Ser Glu Pro Ile Val Leu Phe Asn Leu Gln Ser Ser
                245                 250                 255

Leu Cys Asp Gly Lys Arg Gly Met Phe Val Thr Ser Pro Phe Arg Ser
                260                 265                 270

Asp Lys Val Asn Leu Leu Asp Ile Glu Asp Lys Glu Arg Pro Asn Ser
                275                 280                 285

Glu Lys Asn Trp Ser Pro Phe Phe Leu Asp Asp Val Glu Val Ser Lys
            290                 295                 300

Tyr Ser Thr Gly Tyr Val His Phe Val Tyr Ser Phe Asn Pro Leu Lys
305                 310                 315                 320

Val Ile Lys Cys Ser Leu Asp Thr Gly Ala Cys Arg Met Ile Tyr Glu
                325                 330                 335

Ser Pro Glu Glu Gly Arg Phe Gly Ser Glu Leu Arg Gly Ala Thr Pro
            340                 345                 350

Met Val Lys Leu Pro Val His Leu Ser Leu Pro Lys Gly Lys Glu Val
            355                 360                 365

Trp Val Ala Phe Pro Arg Thr Arg Leu Arg Asp Cys Gly Cys Ser Arg
            370                 375                 380

Thr Thr Tyr Arg Pro Val Leu Thr Leu Phe Val Lys Glu Gly Asn Lys
385                 390                 395                 400

Phe Tyr Thr Glu Leu Ile Ser Ser Ile Asp Phe His Ile Asp Val
            405                 410                 415

Leu Ser Tyr Asp Ala Lys Gly Glu Ser Cys Ser Gly Ser Ile Ser Val
                420                 425                 430

Leu Ile Pro Asn Gly Ile Asp Ser Trp Asp Val Ser Lys Lys Gln Gly
            435                 440                 445

Gly Lys Ser Asp Ile Leu Thr Leu Thr Leu Ser Glu Ala Asp Arg Asn
            450                 455                 460

Thr Val Val His Val Lys Gly Leu Leu Asp Tyr Leu Leu Val Leu
465                 470                 475                 480

Asn Gly Glu Gly Pro Ile His Asp Ser His Ser Phe Lys Asn Val Leu
                485                 490                 495

Ser Thr Asn His Phe Lys Ser Asp Thr Thr Leu Leu Asn Ser Val Lys
                500                 505                 510

Ala Ala Glu Cys Ala Ile Phe Ser Ser Arg Asp Tyr Cys Lys Lys Tyr
```

```
                 515                 520                 525
Gly Glu Thr Arg Gly Glu Pro Ala Arg Tyr Ala Lys Gln Met Glu Asn
            530                 535                 540

Glu Arg Lys Glu Lys Glu Lys Lys Glu Lys Glu Ala Lys Glu Lys Leu
545                 550                 555                 560

Glu Ala Glu Lys Ala Glu Met Glu Glu Ala Val Arg Lys Ala Gln Glu
                565                 570                 575

Ala Ile Ala Gln Lys Glu Arg Glu Lys Glu Ala Glu Gln Glu Lys
            580                 585                 590

Lys Ala Gln Gln Glu Ala Lys Lys Glu Ala Glu Lys Ala Ala
            595                 600                 605

Lys Glu Lys Glu Ala Lys Glu Asn Ala Lys Lys Ile Ile Val
            610                 615                 620

Glu Lys Leu Ala Lys Glu Gln Glu Ala Glu Lys Leu Glu Ala Lys
625                 630                 635                 640

Lys Lys Leu Tyr Gln Leu Gln Glu Glu Glu Arg Ser
                645                 650

<210> SEQ ID NO 14
<211> LENGTH: 594
<212> TYPE: PRT
<213> ORGANISM: Pichia pastoris

<400> SEQUENCE: 14

Met Arg Ile Arg Ser Asn Val Leu Leu Leu Ser Thr Ala Gly Ala Leu
1               5                   10                  15

Ala Leu Val Trp Phe Ala Val Phe Ser Trp Asp Asp Lys Ser Ile
            20                  25                  30

Phe Gly Ile Pro Thr Pro Gly His Ala Val Ala Ser Ala Tyr Asp Ser
            35                  40                  45

Ser Val Thr Leu Gly Thr Phe Asn Asp Met Glu Val Asp Ser Tyr Val
        50                  55                  60

Thr Asn Ile Tyr Asp Asn Ala Pro Val Leu Gly Cys Tyr Asp Leu Ser
65                  70                  75                  80

Tyr His Gly Leu Leu Lys Val Ser Pro Lys His Glu Ile Leu Cys Asp
                85                  90                  95

Met Lys Phe Ile Arg Ala Arg Val Leu Glu Thr Glu Ala Tyr Ala Ala
            100                 105                 110

Leu Lys Asp Leu Glu His Lys Lys Leu Thr Glu Glu Lys Ile Glu
        115                 120                 125

Lys His Trp Phe Thr Phe Tyr Gly Ser Ser Val Phe Leu Pro Asp His
    130                 135                 140

Asp Val His Tyr Leu Val Arg Arg Val Phe Ser Gly Glu Gly Lys
145                 150                 155                 160

Ala Asn Arg Pro Ile Thr Ser Ile Leu Val Ala Gln Ile Tyr Asp Lys
                165                 170                 175

Asn Trp Asn Glu Leu Asn Gly His Phe Leu Asn Val Leu Asn Pro Asn
            180                 185                 190

Thr Gly Lys Leu Gln His His Ala Phe Pro Gln Val Leu Pro Ile Ala
        195                 200                 205

Val Asn Trp Asp Arg Asn Ser Lys Tyr Arg Gly Gln Glu Asp Pro Arg
    210                 215                 220

Val Val Leu Arg Arg Gly Arg Phe Gly Pro Asp Pro Leu Val Met Phe
225                 230                 235                 240
```

```
Asn Thr Leu Thr Gln Asn Asn Lys Leu Arg Arg Leu Phe Thr Ile Ser
                245                 250                 255

Pro Phe Asp Gln Tyr Lys Thr Val Met Tyr Arg Thr Asn Ala Phe Lys
            260                 265                 270

Met Gln Thr Thr Glu Lys Asn Trp Val Pro Phe Phe Leu Lys Asp Asp
        275                 280                 285

Gln Glu Ser Val His Phe Val Tyr Ser Phe Asn Pro Leu Arg Val Leu
    290                 295                 300

Asn Cys Ser Leu Asp Asn Gly Ala Cys Asp Val Leu Phe Glu Leu Pro
305                 310                 315                 320

His Asp Phe Gly Met Ser Ser Glu Leu Arg Gly Ala Thr Pro Met Leu
                325                 330                 335

Asn Leu Pro Gln Ala Ile Pro Met Ala Asp Asp Lys Glu Ile Trp Val
            340                 345                 350

Ser Phe Pro Arg Thr Arg Ile Ser Asp Cys Gly Cys Ser Glu Thr Met
        355                 360                 365

Tyr Arg Pro Met Leu Met Leu Phe Val Arg Glu Gly Thr Asn Phe Phe
    370                 375                 380

Ala Glu Leu Leu Ser Ser Ser Ile Asp Phe Gly Leu Glu Val Ile Pro
385                 390                 395                 400

Tyr Thr Gly Asp Gly Leu Pro Cys Ser Ser Gly Gln Ser Val Leu Ile
                405                 410                 415

Pro Asn Ser Ile Asp Asn Trp Glu Val Thr Gly Ser Asn Gly Glu Asp
            420                 425                 430

Ile Leu Ser Leu Thr Phe Ser Glu Ala Asp Lys Ser Thr Ser Val Val
        435                 440                 445

His Ile Arg Gly Leu Tyr Lys Tyr Leu Ser Glu Leu Asp Gly Tyr Gly
    450                 455                 460

Gly Pro Glu Ala Glu Asp Glu His Asn Phe Gln Arg Ile Leu Ser Asp
465                 470                 475                 480

Leu His Phe Asp Gly Lys Lys Thr Ile Glu Asn Phe Lys Lys Val Gln
                485                 490                 495

Ser Cys Ala Leu Asp Ala Ala Lys Ala Tyr Cys Lys Glu Tyr Gly Val
            500                 505                 510

Thr Arg Gly Glu Glu Asp Arg Leu Lys Asn Lys Glu Lys Glu Arg Lys
        515                 520                 525

Ile Glu Glu Lys Arg Lys Lys Glu Glu Arg Lys Lys Lys Glu Glu
    530                 535                 540

Glu Lys Lys Lys Lys Glu Glu Glu Lys Lys Lys Lys Glu Glu
545                 550                 555                 560

Glu Glu Glu Glu Lys Arg Leu Lys Glu Leu Lys Lys Leu Lys Glu
                565                 570                 575

Leu Gln Glu Glu Leu Glu Lys Gln Lys Asp Glu Val Lys Asp Thr Lys
            580                 585                 590

Ala Lys

<210> SEQ ID NO 15
<211> LENGTH: 503
<212> TYPE: PRT
<213> ORGANISM: Pichia pastoris

<400> SEQUENCE: 15

Met Lys Leu Asp Thr Gln Gln Ile Ser His Leu Leu Ser Arg Gln Met
1               5                   10                  15
```

-continued

```
Tyr His Leu Ala Pro Arg Lys Lys Leu Leu Ile Trp Gly Gly Ser Leu
         20                  25                  30
Gly Phe Val Leu Leu Leu Ile Val Ala Ser Ser His Gln Arg Ile
             35                  40                  45
Arg Ser Thr Ile Leu His Arg Thr Pro Ile Ser Thr Leu Pro Val Ile
 50                  55                  60
Ser Gln Glu Val Ile Thr Ala Asp Tyr His Pro Thr Leu Leu Thr Gly
 65                  70                  75                  80
Phe Ile Pro Thr Asp Ser Asp Ser Asp Cys Ala Asp Phe Ser Pro
                 85                  90                  95
Ser Gly Val Ile Tyr Ser Thr Asp Lys Leu Val Leu His Asp Ser Leu
                100                 105                 110
Lys Asp Ile Arg Asp Ser Leu Leu Lys Thr Gln Tyr Lys Asp Leu Val
                115                 120                 125
Thr Leu Glu Asp Glu Lys Met Asn Ile Asp Asp Ile Leu Lys Arg
130                 135                 140
Trp Tyr Thr Leu Ser Gly Ser Ser Val Trp Ile Pro Gly Met Lys Ala
145                 150                 155                 160
His Leu Val Val Ser Arg Val Met Tyr Leu Gly Thr Asn Gly Arg Ser
                165                 170                 175
Asp Pro Leu Val Ser Phe Val Arg Val Gln Leu Phe Asp Pro Asp Phe
                180                 185                 190
Asn Glu Leu Lys Asp Ile Ala Leu Lys Phe Ser Asp Lys Pro Asp Gly
                195                 200                 205
Thr Val Ile Phe Pro Tyr Ile Leu Pro Val Asp Ile Pro Arg Glu Gly
                210                 215                 220
Ser Arg Trp Leu Gly Pro Glu Asp Ala Lys Ile Ala Val Asn Pro Glu
225                 230                 235                 240
Thr Pro Asp Asp Pro Ile Val Ile Phe Asn Met Gln Asn Ser Val Asn
                245                 250                 255
Arg Ala Met Tyr Gly Phe Tyr Pro Phe Arg Pro Glu Asn Lys Gln Val
                260                 265                 270
Leu Phe Ser Ile Lys Asp Glu Glu Pro Arg Lys Lys Glu Lys Asn Trp
                275                 280                 285
Thr Pro Phe Phe Val Pro Gly Ser Pro Thr Thr Val Asn Phe Val Tyr
                290                 295                 300
Asp Leu Gln Lys Leu Thr Ile Leu Lys Cys Ser Ile Thr Gly Ile
305                 310                 315                 320
Cys Glu Lys Glu Phe Val Ser Gly Asp Gly Gln Asn His Gly Ile
                325                 330                 335
Gly Ile Phe Arg Gly Gly Ser Asn Leu Val Pro Phe Pro Thr Ser Phe
                340                 345                 350
Thr Asp Lys Asp Val Trp Val Gly Phe Pro Lys Thr His Met Glu Ser
                355                 360                 365
Cys Gly Cys Ser Ser His Ile Tyr Arg Pro Tyr Leu Met Val Leu Val
370                 375                 380
Arg Lys Gly Asp Phe Tyr Tyr Lys Ala Phe Val Ser Thr Pro Leu Asp
385                 390                 395                 400
Phe Gly Ile Asp Val Arg Ser Trp Glu Ser Ala Glu Ser Thr Ser Cys
                405                 410                 415
Gln Thr Ala Lys Asn Val Leu Ala Val Asn Ser Ile Ser Asn Trp Asp
                420                 425                 430
Leu Leu Asp Asp Gly Leu Asp Lys Asp Tyr Met Thr Ile Thr Leu Ser
```

-continued

```
            435                 440                 445
Glu Ala Asp Val Val Asn Ser Val Leu Arg Val Arg Gly Ile Ala Lys
        450                 455                 460

Phe Val Asp Asn Leu Thr Met Asp Asp Gly Ser Thr Thr Leu Ser Thr
465                 470                 475                 480

Ser Asn Lys Ile Asp Glu Cys Ala Thr Thr Gly Ser Lys Gln Tyr Cys
                485                 490                 495

Gln Arg Tyr Gly Glu Leu His
            500
```